United States Patent
Miyota et al.

(10) Patent No.: US 6,372,921 B1
(45) Date of Patent: Apr. 16, 2002

(54) PROCESS FOR PRODUCING ISOCHROMANONES AND INTERMEDIATES THEREOF

(75) Inventors: Yoshiaki Miyota; Akira Shibuya; Masaru Yasuda; Kimitaka Ohshiro; Makoto Saito, all of Kanagawa (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/444,309

(22) Filed: Nov. 22, 1999

Related U.S. Application Data

(60) Provisional application No. 60/136,026, filed on May 25, 1999, provisional application No. 60/136,027, filed on May 25, 1999, provisional application No. 60/136,029, filed on May 25, 1999, and provisional application No. 60/136,137, filed on May 25, 1999.

(30) Foreign Application Priority Data

| Feb. 1, 1999 | (JP) | 11-024299 |
| Feb. 1, 1999 | (JP) | 11-024300 |
| May 25, 1999 | (JP) | 11-144592 |
| May 25, 1999 | (JP) | 11-144653 |

(51) Int. Cl.$^7$ ................ C07D 311/76; C07C 255/00
(52) U.S. Cl. ................ 549/290; 558/388; 568/811; 568/812
(58) Field of Search ................ 549/289, 290; 558/388; 568/811, 812

(56) References Cited

FOREIGN PATENT DOCUMENTS

| JP | 01026528 | 1/1989 | ........... C07C/33/26 |
| JP | 09067364 | 3/1997 | ......... C07D/311/76 |

OTHER PUBLICATIONS

Research Disclosure, May 10, 1998, pp. 581–584.

*Primary Examiner*—Amelia Owens
(74) *Attorney, Agent, or Firm*—Sughrue Mion, PLLC

(57) ABSTRACT

(1) Methods for producing isochromanone compounds from o-xylene compounds as starting compounds through α-halogeno-o-xylene derivatives, α-cyano-o-xylene derivatives, and α-halogeno-α'-cyano-o-xylene derivatives, and (2) methods for producing isochromanone compounds from o-xylene compounds as starting compounds through α,α'-dihalogeno-o-xylene derivatives, α,α'-dihydroxy-o-xylene derivatives, α-halogeno-α'-hydroxy-o-xylene derivatives and α-cyano-α'-hydroxy-o-xylene derivatives, and methods for producing these intermediate compounds.

34 Claims, No Drawings

PROCESS FOR PRODUCING ISOCHROMANONES AND INTERMEDIATES THEREOF

CROSS REFERENCE TO THE RELATED APPLICATIONS

This is an application based on the prescription of 35 U.S.C. Section 111(a) with claiming the benefit of filing dates of U.S. Provisional applications Serial Nos. 60/136,026, 60/136,027, 60/136,029, and 60/136,137, each filed on May 25, 1999 under the provision of 35 U.S.C.111(b), pursuant to 35 U.S.C. Section 119(e)(i).

TECHNICAL FIELD

The present invention relates to methods for producing isochromanone compounds useful as raw materials for drugs and agricultural chemicals and to methods for producing intermediate compounds for the production of isochromanone compounds. More particularly, the present invention relates to (1) methods for producing isochromanone compounds from o-xylene compounds as starting compounds through α-halogeno-o-xylene derivatives, α-cyano-o-xylene derivatives, and α-halogeno-α'-cyano-o-xylene derivatives, and (2) methods for producing isochromanone compounds from o-xylene compounds as starting compounds through α,α'-dihalogeno-o-xylene derivatives, α,α'-dihydroxy-o-xylene derivatives, α-halogeno-α'-hydroxy-o-xylene derivatives and α-cyano-α'-hydroxy-o-xylene derivatives, and (3) methods for producing these intermediates for the production of isochromanone compounds.

BACKGROUND ART (1) As a general method for producing α-halogeno-o-xylene compounds, various methods have heretofore been known. For example, in the case of α-chloro-o-xylene, there have been known a reaction of o-xylene as a starting compound with N-halogenated succinimide and a reaction of o-xylene as a starting compound with sulfuryl chloride or chlorine in the presence of azobisisobutyronitrile (AIBN).

Also, a method for selectively producing of α-chloro-o-xylene by reaction of 2-methylbenzyl alcohol (α-hydroxy-o-xylene) with thionyl chloride has been known (J. Am. Chem. Soc., 62, 2295 (1940)).

Of these methods, the method in which o-xylene and chlorine are reacted tends to give di- or tri-substituted perchlorides and it is difficult to obtain only α-chloro-o-xylene selectively.

The method in which 2-methylbenzyl alcohol and thionyl chloride are reacted by-produces highly toxic sulfurous acid gas and hence is undesirable as a commercial method.

Thus, conventional production methods for α-halogeno-o-xylene compounds produce highly toxic by-products or the target product, α-halogeno-o-xylene, has low selectivity so that they are not always satisfactory methods for practicing on an industrial scale.

(2) Production methods for α,α'-dihydroxy-o-xylene compounds include a method in which α,α'-dibromo-o-xylene is heated in the presence of sodium hydroxide to obtain α,α'-dihydroxy-o-xylene (Ber., 17, 123 (1884)). α,α'-Dihydroxy-o-xylene is under alkaline condition and when heated, an intermediate α-hydroxy-α'-halogeno-o-xylene undergoes intramolecular dehalogenohydrogenation to produce phthalan of formula (XI) and the yield of objective α,α'-dihydroxy-o-xylene decreases so that the method is not suitable for industrial application.

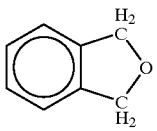

(XI)

Similarly, a method has been reported in which α,α'-dibromo-o-xylene is hydrolyzed in the presence of potassium hydroxide to obtain α,α'-dihydroxy-o-xylene (Ann. Chim. Phys., [6]6, 106 (1885)). Similarly, phthalan is produced and is not advantageous for industrial application.

Further, a method in which o-phthaloyl dichloride is converted to α,α'-dihydroxy-o-xylene with sodium amalgam (Ber., 12, 646 (1879)), a method in which phthalic anhydride or o-phthaloyl dichloride is reduced with lithium aluminum hydride (LiAlH$_4$)to synthesize α,α'-dihydroxy-o-xylene (Nystrom et al., J. Am. Chem. Soc., 69, 1197–9 (1947)), a method in which o-phthaloyl dichloride is reacted with sodium borohydride (NaBH$_4$) in dioxane to obtain α,α'-dihydroxy-o-xylene (Chaikin et al., J. Am. Chem. Soc., 71, 122–5 (1949)) are known. In each case, starting compounds are not available industrially so that they are not industrially advantageous.

Further, there is disclosed a method for producing a,α'-dihydroxy-o-xylene in which α,α'-dichloro-o-xylene is reacted with water in the presence of an alkali metal formate or alkaline earth metal formate (JP-A-64-26528). Addition of formate necessitates disposal of formic acid after ultimately recovering α,α'-dihydroxy-o-xylene. That is, there occurs mixing of formic acid, which is a BOD source, into wastewater so that treatment of wastewater becomes necessary, making the process complicated.

(3) There have been few report on the production method for α-halogeno-α'-cyano-o-xylenes. An example of reports is Research Disclosure (RD) 409066, p.581–584. This discloses synthesis of α-chloro-α'-cyano-o-xylene by reacting α-cyano-o-xylene with sulfuryl chloride in fluorobenzene as a solvent. However, the method uses sulfuryl chloride, which is expensive, as a chlorinating agent and is unsatisfactory as an industrial method.

(4) The production method for α-halogeno-α'-hydroxy-xylenes is reported in J. Org. Chem., 57, 4074–4079 (1992). In this production method, α,α'-dihydroxy-xylene is reacted with thionyl chloride using benzene as a solvent and pyridine as a catalyst. However, this method requires overnight reaction time and yield of the reaction is as low as 59.5% so that it is not advantageous for industrial application.

(5) α-Carboxy-α'-hydroxy-xylenes and salts thereof are industrially useful compounds. However, there are few industrial production methods.

On the production method for α-carboxy-α'-hydroxy-xylenes and salts thereof, JP-A-9-67364 describes that trial to synthesize them through α-carboxy-α'-hydroxy-o-xylene by reacting α,α'-dihalogeno-o-xylene with carbon monoxide and water in the presence of a catalyst such as palladium failed since α-carboxy-α'-hydroxy-o-xylene was not synthesized.

Regarding α,α'-dihalogeno-m-xylene or α,α'-dihalogeno-p-xylene, it is considered that α-carboxy-α'-hydroxy-xylenes can be synthesized therefrom similarly to the method described in JP-A-9-67364. However, use of expensive catalysts is required so that such a method is not an industrially advantageous method.

(6) Regarding 3-isochromanone, there is a report that it can be synthesized by reacting o-bromomethylbenzyl alcohol (α-bromo-o-xylene) with carbon monoxide in the presence of palladium complex catalyst (J. Am. Chem. Soc., 102, 4191 (1908)). However, use of expensive catalysts does not make the method industrially advantageous.

Further, Research Disclosure (RD) 409066, p.581–584 discloses a method in which 3-isochromanone is produced using α-chloro-α'-cyano-o-xylenes as raw material and large excess sulfuric acid and tetrabutylammonium bromide. This method uses a large amount of sulfuric acid and hence produces a large amount of wastewater, thus raising the problems of imposing a large load on the environment and low yields.

Further, as another method, a method has been known in which α-halogeno-α'-cyano-o-xylenes are subjected to alkali hydrolysis in an aqueous solution of sodium hydroxide or potassium hydroxide, and the reaction mixture is rendered acidic by addition of acid to cyclize them. This method requires two reaction processes, i.e., the alkali hydrolysis of α-halogeno-α'-cyano-o-xylenes (hydrolysis reaction step) and then acidification with acid (cyclizing step), resulting in that yield is too low for the method to be adopted industrially.

PROBLEMS WHICH THE INVENTION IS TO SOLVE

A main object of the present invention is to provide an industrially advantageous production method that can efficiently give 3-isochromanone compounds from o-xylene compounds as raw materials.

More particularly, an object of the present invention is to use o-xylene compounds as raw materials and provide:

(1) an industrially advantageous production method for isochromanone compounds through α-halogeno-o-xylene derivatives, α-cyano-o-xylene derivatives, and α-halogeno-α'-cyano-o-xylene derivatives.

Also, an object of the present invention is to use o-xylene compounds as raw materials and provide: (2) an industrially advantageous production method for isochromanone compounds through α,α'-dihalogeno-o-xylene derivatives, α,α'-dihydroxy-o-xylene derivatives, and α-halogeno-α'-cyano-o-xylene derivatives, or α-cyano-α'-hydroxy-o-xylene derivatives.

Further, other object of the present invention is to provide novel production method for α-chloro-o-xylene compounds, α,α'-dihydroxy-o-xylene compounds, α-halogeno-α'-hydroxy-o-xylene compounds, and α-chloro-α'-cyano-o-xylene compounds, which are intermediates for the production methods for isochromanone compounds in (1) and (2) above.

DISCLOSURE OF THE INVENTION

The present invention relates to a production method for the following isochromanone compounds, a production method for α-halogeno-α'-cyano-o-xylene compounds, a production method for α-cyano-α'-hydroxy-o-xylene compounds, a production method for α-halogeno-α'-hydroxy-o-xylene compounds, and a production method for α,α'-dihydroxy-o-xylene compounds.

(1) A method for producing isochromanone compound of formula (V)

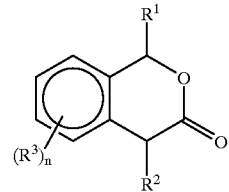

(wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different), which comprises the steps of:

subjecting an o-xylene compound of formula (I)

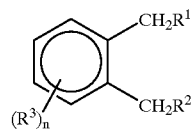

(wherein the symbols have the same meanings as defined above) to halogenation reaction in gas phase or liquid phase to prepare an α-halogeno-o-xylene compound of formula (II)

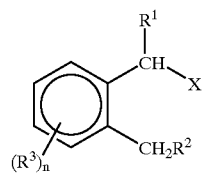

(wherein X represents a halogen atom, and other symbols have the same meanings as defined above);

reacting the compound of formula (II) above with hydrogen cyanide or salts thereof to prepare an α-cyano-o-xylene compound of formula (III)

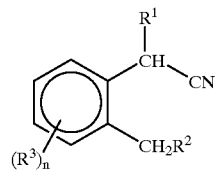

(wherein the symbols have the same meanings as defined above);

reacting the compound of formula (III) with halogen to prepare an α-halogeno-α'-cyano-o-xylene compound of formula (IV)

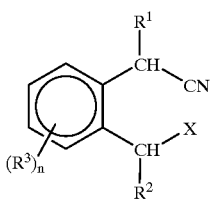

(IV)

(wherein the symbols have the same meanings as defined above); and hydrolyzing the compound of formula (IV) in water or water containing a protic polar solvent under acidic condition.

(2) A method for producing isochromanone compound of formula (V)

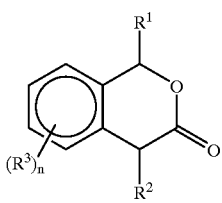

(V)

(wherein the symbols have the same meanings as defined above), which comprises the step of:

hydrolyzing an α-halogeno-α'-cyano-o-xylene of formula (IV)

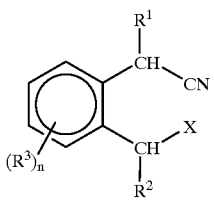

(IV)

(wherein the symbols have the same meanings as defined above) in water or water containing a protic polar solvent under acidic condition.

(3) The method for producing isochromanone compound as described in (2) above, wherein the protic polar solvent is lower alcohol.

(4) The method for producing isochromanone compound as described in (2) above, wherein an inorganic acid and/or a metal chloride are added and hydrolysis reaction is carried out.

(5) The method for producing isochromanone compound as described in (4) above, wherein the metal chloride is aluminum chloride or zinc chloride.

(6) The method for producing isochromanone compound as described in (4) above, wherein addition amount of the inorganic acid and/or metal chloride is 0.1 to 5 equivalents per α-halogeno-α'-cyano-o-xylene compound.

(7) The method for producing isochromanone compound as described in (2) above, wherein the hydrolysis reaction is carried out under heating conditions at 70 to 200° C.

(8) The method for producing isochromanone compound as described in (2) above, wherein the hydrolysis reaction is carried out under pressurized conditions at atmospheric pressure to 20 kg/cm$^2$.

(9) The method for producing isochromanone compound as described in (2) above, wherein the α-halogeno-α'-cyano-o-xylene compound of formula (IV) is α-chloro-α'-cyano-o-xylene and the isochromanone compound of formula (V) is 3-isochromanone.

(10) A method for producing α-halogeno-α'-cyano-o-xylene compound of formula (IV)

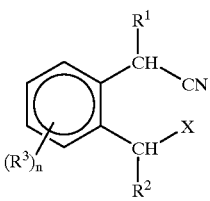

(IV)

(wherein the symbols have the same meanings as defined in (1) above) comprising the step of:

reacting an α-cyano-o-xylene compound of formula (III)

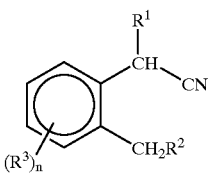

(III)

(wherein the symbols have the same meanings as defined above) with halogen.

(11) The method for producing α-halogeno-α'-cyano-o-xylene compound as described in (10) above, wherein the α-cyano-o-xylene compound is diluted with an organic solvent and reaction is carried out in liquid phase.

(12) The method for producing α-halogeno-α'-cyano-o-xylene compound as described in (10) above, wherein the reaction is carried out in the presence of a radical initiator or under irradiation of ultraviolet rays.

(13) The method for producing α-halogeno-α'-cyano-o-xylene compound as described in (10) above, wherein the α-cyano-o-xylene compound is vaporized and the reaction is carried out in gas phase.

(14) The method for producing α-halogeno-α'-cyano-o-xylene compound as described in (10) above, wherein the α-cyano-o-xylene compound is α-cyano-o-xylene and the α-halogeno-α'-cyano-o-xylene compound is α-halogeno-α'-cyano-o-xylene.

(15) A method for producing isochromanone compound of formula (V)

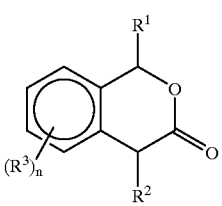

(V)

(wherein R$^1$ and R$^2$ independently of each other represent hydrogen atom or an alkyl group, R$^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different), which comprises the steps of:

subjecting an o-xylene compound of formula (I)

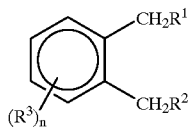

(I)

(wherein the symbols have the same meanings as defined above) to halogenation reaction in gas phase or liquid phase to prepare an α,α'-dihalogeno-o-xylene compound of formula (VI)

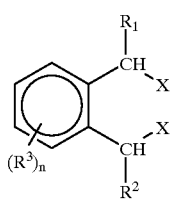

(VI)

(wherein X represents a halogen atom, and other symbols have the same meanings as defined above);

heating the compound of (VI) in the presence of water at pH 8 or lower to prepare an α,α'-dihydroxy-o-xylene compound of formula of formula (VII)

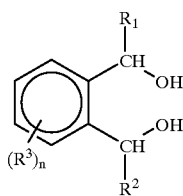

(VII)

(wherein the symbols have the same meanings as defined above);

reacting the compound of formula (VII) with hydrogen halide to prepare an α-halogeno-α'-hydroxy-o-xylene compound of formula (VIII)

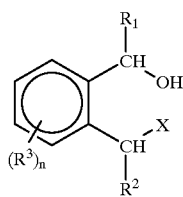

(VIII)

(wherein the symbols have the same meanings as defined above);

reacting the compound of formula (VIII) with hydrogen cyanide or salts thereof to prepare an α-cyano-α'-hydroxy-o-xylene compound of formula (IX)

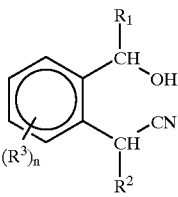

(IX)

(wherein the symbols have the same meanings as defined above); and acid hydrolyzing the compound of formula (IX).

(16) A method for producing an isochromanone compound of formula (V)

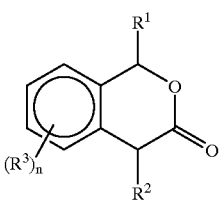

(V)

(wherein the symbols have the same meanings as defined in (15) above), comprising the step of:

acid hydrolyzing a compound of formula (IX)

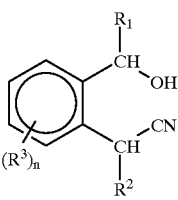

(IX)

(wherein the symbols have the same meanings as defined above).

(17) The method for producing an isochromanone compound as described in (16) above, wherein an α-cyano-α'-hydroxy-o-xylene compound of formula (IX)

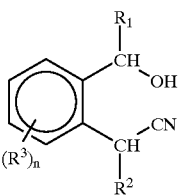

(IX)

(wherein the symbols have the same meanings as defined in (15) above) obtained by reacting a compound of formula (VIII)

(VIII)

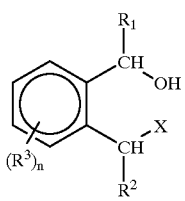

(wherein the symbols have the same meanings as defined above) with hydrogen cyanide or salts thereof is used.

(18) A method for producing an α-cyano-α'-hydroxy-o-xylene compound of formula (IX)

(IX)

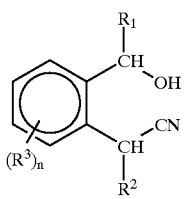

(wherein the symbols have the same meanings as defined in (15) above), comprising the step of:

reacting an α-halogeno-α'-hydroxy-o-xylene compound of formula (VIII)

(VIII)

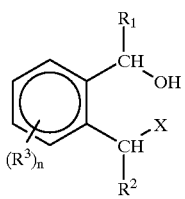

(wherein the symbols have the same meanings as defined above) with hydrogen cyanide or salts thereof.

(19) The method for producing an α-cyano-α'-hydroxy-o-xylene compound as described in (18) above, wherein an α-halogeno-α'-hydroxy-o-xylene compound of formula (VIII) obtained by reacting a compound of formula (VII)

(VII)

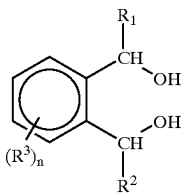

(wherein the symbols have the same meanings as defined above) with hydrogen halide is used.

(20) The method for producing an α-cyano-α'-hydroxy-o-xylene compound as described in (18) above, wherein hydrogen cyanide or salts thereof are reacted at a pH in the range of 4 to 10.

(21) The method for producing an α-cyano-α'-hydroxy-o-xylene compound as described in (18) above, wherein hydrogen cyanide or salts thereof are reacted by addition of a phase transfer catalyst.

(22) The method for producing an α-cyano-α'-hydroxy-o-xylene compound as described in (18) above, wherein the α-halogeno-α'-hydroxy-o-xylene compound is α-halogeno-α'-hydroxy-o-xylene.

(23) A method for producing an α-halogeno-α'-hydroxy-o-xylene compound of formula (VIII)

(VIII)

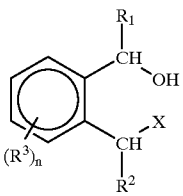

(wherein the symbols have the same meanings as defined in (15) above), comprising the step of reacting a α,α'-dihydroxy-o-xylene compound of formula (VII)

(VII)

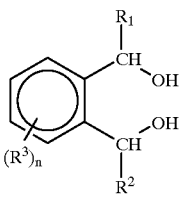

(wherein the symbols have the same meanings as defined above) with hydrogen halide.

(24) The method for producing an α-halogeno-α'-hydroxy-o-xylene compound as described in (23) above, wherein the reaction is carried out in an aqueous solution.

(25) The method for producing an α-halogeno-α'-hydroxy-o-xylene compound as described in (24) above, wherein a hydrophobic organic solvent is used together.

(26) The method for producing an α-halogeno-α'-hydroxy-o-xylene compound as described in (24) above, wherein water is used 5 to 15 folds by mole based on the α,α'-dihydroxy-o-xylene compound.

(27) The method for producing an α-halogeno-α'-hydroxy-o-xylene compound as described in (23) above, wherein for the reaction, the hydrogen halide is used 1.5 to 3 folds by mole based on the α,α'-dihydroxy-o-xylene compound.

(28) The method for producing an α-halogeno-α'-hydroxy-o-xylene compound as described in (23) above, wherein the hydrogen halide is hydrogen chloride.

(29) The method for producing an α-halogeno-α'-hydroxy-o-xylene compound as described in (23) above, wherein the α,α'-dihydroxy-o-xylene compound of formula (VII) is α,α'-dihydroxy-o-xylene and the α-halogeno-α'-hydroxy-o-xylene compound of formula (VIII) is α-chloro-α'-hydroxy-o-xylene.

(30) A method for producing an α,α'-dihydroxy-o-xylene compound of formula (VII)

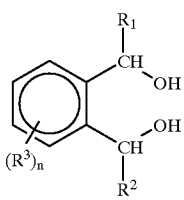

(VII)

(wherein the symbols have the same meanings as defined in (15) above), comprising the step of:

heating an α,α'-dihalogeno-o-xylene compound of formula (VI)

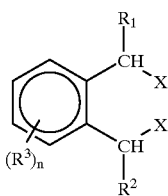

(VI)

(wherein the symbols have the same meanings as defined above) at pH 8 or less in the presence of water.

(31) The method for producing an α,α'-dihydroxy-o-xylene compound as described in (30) above, wherein the reaction is carried out at pH 8 or lower.

(32) The method for producing an α,α'-dihydroxy-o-xylene compound as described in (30) above, wherein water is 10 folds by weight or more based on the α,α'-dihalogeno-o-xylene compound.

(33) The method for producing an α,α'-dihydroxy-o-xylene compound as described in (30) above, wherein the reaction is carried out in an aqueous solution.

(34) The method for producing an α,α'-dihydroxy-o-xylene compound as described in (30) above, wherein the α,α'-dihalogeno-o-xylene compound of formula (VI) is α,α'-dichloro-o-xylene and the α,α'-dihydroxy-o-xylene compound of formula (VIII) is α,α'-dihydroxy-o-xylene.

Further, the present invention relates to the following production method for α-halogeno-o-xylene compounds, production method for α-carboxy-α'-hydroxy-o-xylene compounds, and production method for isochromanone compounds.

(35) A method for producing α-halogeno-o-xylene compound from o-xylene compound by photohalogenation reaction under conditions of reduced pressure in gas phase at 50° C. or higher and 300° C. or lower, wherein conversion of o-xylene compound is controlled to 20% or higher and 50% or lower.

(36) The method for producing α-halogeno-o-xylene compound as described in (35) above, wherein halogen or a mixed gas composed of halogen and inert gas is blown into liquid state o-xylene compound and the o-xylene compound is evaporated at a temperature of not higher than boiling point for use in the reaction.

(37) The method for producing α-halogeno-o-xylene compound as described in (36) or (37) above, wherein the feed rate (mole/hour) of halogen to the feed rate of o-xylene compound is 0.1 or higher and 1.8 or lower.

(38) The method for producing α-halogeno-o-xylene compound as described in any of (35) to (37) above, wherein after the reaction, unreacted o-xylene compound is recovered and reused.

(39) A method for producing α-halogeno-o-xylene compound by reacting an o-xylene compound with halogen by radical reaction in liquid phase, wherein the conversion of o-xylene compound after the reaction is controlled in the range of 20% or higher and 70% or lower.

(40) The method for producing α-halogeno-o-xylene compound as described in (39) above, wherein the o-xylene compound is diluted with an organic solvent and the reaction is carried out.

(41) The method for producing α-halogeno-o-xylene compound as described in (39) or (40) above, wherein the reaction is carried out in the presence of a radical initiator or under irradiation of ultraviolet rays.

(42) The method for producing α-halogeno-o-xylene compound as described in any of (39) to (41) above, wherein the reaction temperature is 50° C. or higher and 150° C. or lower.

(43) The method for producing α-halogeno-o-xylene compound as described in any of (39) to (42) above, wherein the feed rate (mole/hour) of halogen to the feed rate of o-xylene compound is 0.1 or higher and 3 or lower.

(44) The method for producing α-halogeno-o-xylene compound as described in any of (39) to (43) above, wherein the solvent used for reaction is at least one solvent selected from the group consisting of carbon tetrachloride, 1,2-dichloroethane, trichloroethane, benzene, chlorobenzene, fluorobenzene, and cyclohexane.

(45) The method for producing α-halogeno-o-xylene compound as described in any of (39) to (44) above, wherein after the reaction, unreacted o-xylene compound is recovered and reused as a raw material.

(46) The method for producing α-halogeno-o-xylene compound as described in any of (34) to (45) above, wherein the halogen is chlorine and the α-halogeno-o-xylene compound is α-chloro-o-xylene.

(47) A method for producing α-carboxy-α'-hydroxy-o-xylene compound, comprising the step of:

hydrolyzing the α-cyano-α'-hydroxy-o-xylene compound as described in (22) above at pH 11 or higher.

(48) The method for producing α-carboxy-α'-hydroxy-o-xylene compound as described in (47) above, wherein the α-cyano-α'-hydroxy-o-xylene compound obtained by the method described in any of (18) to (22) above is hydrolyzed.

(49) The method for producing α-carboxy-α'-hydroxy-o-xylene compound as described in (47) or (48) above, wherein the α-cyano-α'-hydroxy-o-xylene compound is α-cyano-α'-hydroxy-o-xylene.

(50) A method for producing isochromanone compound, comprising the step of:

heating a metal salt of the α-carboxy-α'-hydroxy-o-xylene compound obtained by the production method as described in (49) at pH 4 or lower.

DETAILED DESCRIPTION OF THE INVENTION

The reaction scheme of the production method for isochromanone compound according to the present invention using an o-xylene compound as a raw material will be shown in Reaction Scheme 1 and Reaction Scheme 2 below.

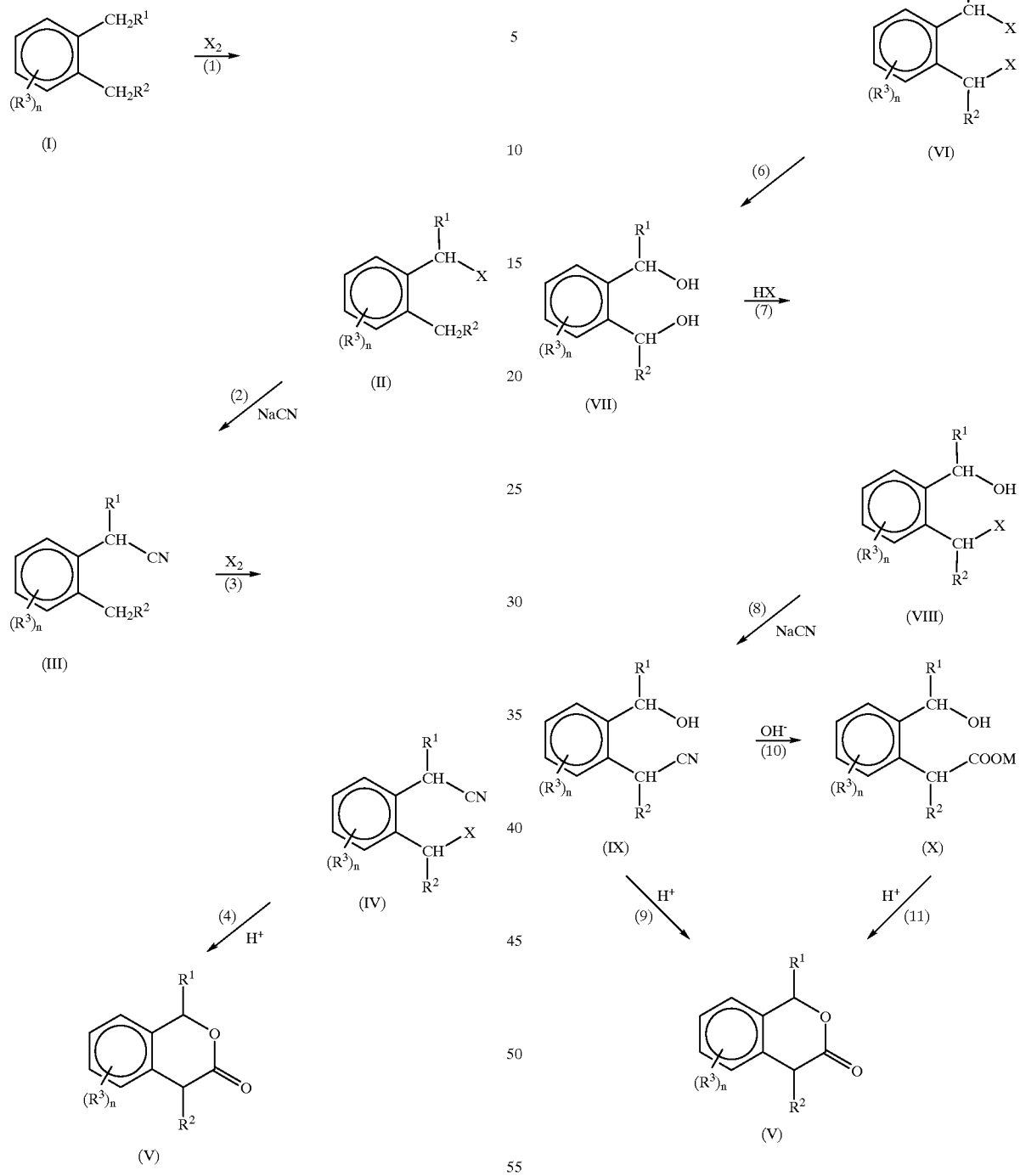

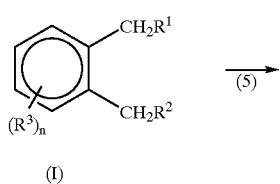

According to Reaction Scheme 1, the reaction starts from the o-xylene compound (I) to reach the isochromanone compound (V) through α-halogeno-o-xylene compound (II), α-cyano-o-xylene compound (III), and α-halogeno-α'-cyano-o-xylene compound (IV).

In the reaction according to Reaction Scheme 2, o-xylene compound (I) is converted through α,α'-dihalogeno-o-xylene compound (VI), α,α'-dihydroxy-o-xylene compound (VII), and α-halogeno-α'-hydroxy-o-xylene compound (VIII) to α-cyano-α'-hydroxy-o-xylene compound (IX). The resultant compound (IX) is derived (i) directly to isochoromanone compound (V) by hydrolysis with acid, or to (ii)

alkali metal salt (X) of α-carboxy-α'-hydroxy-o-xylene compound by alkali hydrolysis and then this is subjected to intramolecular esterification reaction to derive it to isochromanone compound (V).

Hereinafter, the reactions according to Reaction Schemes 1 and 2, respectively, will be explained in order of steps.

Reaction Scheme 1

Step 1: Production Method for α-halogeno-o-xylene Compound (Preparation of compound of formula (II) from compound of formula (I))

The raw material to be used, o-xylenes, are represented by formula (I)

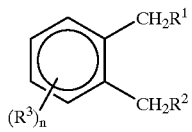

(I)

In the formula, $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different.

Hereinafter, taking the case of α-chlorination of o-xylene which is an inexpensively available industrial material as a specific example of compounds of formula (I), production methods in gas phase and liquid phase that can give α-chloro-o-xylene with high selectivity will be explained.

Reaction in Gas Phase

In the present step, the reaction method in gas phase is carried out by heating o-xylene as a raw material to vaporize, continuously introducing the resultant gas together with chlorine gas to a reactor. While irradiating ultraviolet rays to the mixed gas composed of o-xylene and chlorine, the reaction is carried out. The mixed gas containing α-chloro-o-xylene after the reaction is discharged from the reactor and is cooled in a heat exchanger to obtain a liquefied reaction product. This is sampled, analyzed and the conversion (%) of o-xylene is obtained by the following equation (1).

$$\text{Conversion} = \{(\text{mol of o-xylene before the reaction} - \text{mol of o-xylene after the reaction}) \div (\text{mol of o-xylene before the reaction})\} \times 100$$

In the method of the present step, the feed rate of raw material, the ratio of o-xylene to chlorine and/or reaction temperature are adjusted such that the above conversion of o-xylene is in the range of 20% or higher and 50% or lower.

The reaction in the present step may be at atmospheric pressure or under reduced pressure. When the reaction is too vigorous, reaction may be carried out after the reaction mixture is diluted with inert gas that gives no influence to the reaction, such as argon or nitrogen.

The vaporization of raw material, o-xylene, may be carried out only by heating or by blowing gas such as chlorine gas or inert gas into o-xylene liquid to vaporize it. When the reaction temperature is set at low temperatures, or it is desired to vaporize o-xylene at low temperatures, the method of blowing gas into liquid o-xylene is preferred. Also, o-xylene may be vaporized at temperatures below its boiling point by placing it under reduced pressure.

In the reaction of the present invention, the conversion of o-xylene below 20% is undesirable since productivity is low. On the other hand, the conversion of o-xylene above 50% is undesirable since perchlorinated products such as α,α'-dichloro-o-xylene increase so that the selectivity of α-chloro-o-xylene is decreased. Here, selectivity (%) is defined by the following equation (2):

$$\text{Selectivity} = \{(\text{mol of α-chloro-o-xylene after the reaction}) \div (\text{mol of consumed o-xylene})\} \times 100 \quad (2)$$

The o-xylene contained in the reaction product unreacted without being converted into α-chloro-o-xylene can be recovered by distilling the reaction product and reused as a raw material for producing α-chloro-o-xylene.

The feed rate (mole/hour) of chlorine gas to the feed rate (mole/hour) of o-xylene to be fed is preferably in the range of 0.1 to 4.0. The ratio of chlorine of 4 or higher is undesirable since the amount of chlorine remaining unreacted in the gas after the reaction increases.

Reaction in Liquid Phase

The reaction method in liquid phase is carried out by charging o-xylene or o-xylene diluted with a solvent in a reactor, adding a radical initiator such as azobisisobutyronitrile (AIBN) or by irradiating ultraviolet rays to the reaction solution while blowing chlorine gas. The reaction mixture is sampled and unreacted o-xylene is analyzed. The conversion of o-xylene is obtained by the equation (1) above.

When the conversion of o-xylene reached in the range of 20 to 70%, the blowing of chlorine gas is stopped to terminate the reaction.

The radical initiator used in the present invention may be any one that is generally used usually as radical initiator. Azobis compounds such as AIBN, peroxides such as t-butyl peroxide and benzoyl peroxide, phenylazotriphenylmethane, etc. are used preferably.

The reaction in liquid phase may be run without solvents. When solvents are used, it is advantageous to dilute o-xylene in a concentration by weight of 5 to 80% before it is reacted. If the concentration of o-xylene is lower than 5%, a large amount of solvent is to be used and the concentration of product is low, resulting in low productivity. If the concentration of o-xylene is higher than 80%, perchlorinated products such as α,α'-dichloro-o-xylene are produced to lower not only the selectivity but also yield of the target α-chloro-o-xylene. Here, the selectivity of α-chloro-o-xylene is obtained by the above equation (2).

Generally, the solvent is not particularly limited so far as it does not adversely affect radical substitution reaction. For example, halogenated carbon solvents (carbon tetrachloride, dichloromethane, chloroform, dichloroethane, trichloroethane, hexachloroethane, perfluorohexane, perfluorocyclohexane), hydrocarbon solvents (cyclohexane, hexane), aromatic solvents (benzene, fluorobenzenes, chlorobenzenes, trifluoromethylbenzenes, trichloromethylbenzenes), etc. can be used.

The reaction is terminated when the conversion of o-xylene falls in the range of 20 to 70%. The conversion of xylenes of below 20% is undesirable since productivity is low although the selectivity of α-chloro-o-xylene is high. The conversion of o-xylene above 70% is undesirable since perchlorinated products such as α,α'-dichloro-o-xylene increase to lower the selectivity of α-chloro-o-xylene.

After completion of the reaction, the raw material o-xylene which remains in the reaction product unreacted without being chlorinated can be recovered by distillation, etc. and reused as a raw material for the production of α-chloro-o-xylene.

In the present invention, the feed rate (mol/hour) of chlorine to that of o-xylene to be fed is preferably 0.1 to 3. The ratio of chlorine of below 0.1 is undesirable since it makes the reaction to take a longer time. The ratio of above 3 is also undesirable since the amount of chlorine gas discharged in an unreacted state to the outside the system increases.

The α-chloro-o-xylene produced in the present reaction can give α-chloro-o-xylene containing less impurities such as α,α'-dichloro-o-xylene merely by heating the reaction mixture after the completion of reaction at atmospheric pressure or under reduced pressure to distill off the solvent and unreacted o-xylene to concentrate. If a further purified α-chloro-o-xylene is desired, it can be purified by distillation, etc.

Step 2: Production Method for α-cyano-o-xylene Compound (Preparation of compound of formula (III) from compound of formula (II))

By reaction of an α-halogeno-o-xylene compound of formula (II)

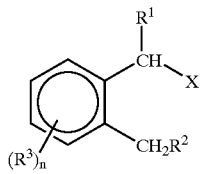

(II)

(wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, ($R^3$)s may be the same or different) with a cyanidating agent such as sodium cyanide, an α-cyano-o-xylene compound of formula (III)

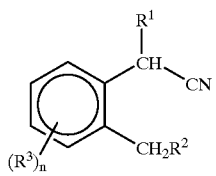

(III)

(wherein the symbols have the same meanings as defined above) can be synthesized.

That is, the production method of α-cyano-o-xylene compound (II) is carried out by adding 1 equivalent or more of an aqueous sodium cyanide solution to an α-halogeno-o-xylene compound in the presence of a phase transfer catalyst such as tetrabutylammonium bromide and heating with stirring to perform the reaction. The reaction mixture is separated into two layers and the organic layer is recovered. Then, to remove moisture in the organic layer, a drying agent such as calcium chloride is used or water is distilled off to obtain α-cyano-o-xylenes which can be used as a raw material for the production in the present invention.

Step 3: Production Method for α-halogeno-α'-cyano-o-xylene Compound (Preparation of compound of formula (IV) from compound of formula (III))

By reaction of the α-cyano-o-xylene compound of formula (III) obtained in the above Step 2 with halogen α-halogeno-α'-cyano-o-xylenes of formula (IV)

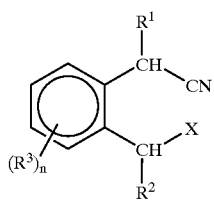

(IV)

(wherein $R^1$, $R^2$, and $R^3$ have the same meanings as defined above and X represents a halogen atom) can be produced.

When the reaction is carried out in liquid phase, an α-cyano-o-xylene in a liquid state or diluted with a solvent is charged in a reactor and halogen gas is blown into the liquid for reaction in the presence of a radical initiator such as AIBN or under the condition of irradiation with ultraviolet rays. The radical initiator includes besides AIBN t-butyl peroxide, benzoyl peroxide, phenylazotriphenylmethane, etc. However, it is not particularly limited and any one may be used so far as it serves as a radical initiator. In this case, solvents may or need not be used. Preferably, α-cyano-o-xylene is diluted in a concentration by weight of 5 to 80% before it is reacted. If the concentration of α-cyano-o-xylene is lower than 5%, productivity is too low for an industrial process. If the concentration of α-cyano-o-xylene is higher than 80%, the selectivity of α-halogeno-α'-cyano-o-xylenes becomes lower resulting in low yield of the target compound. Generally, the solvent is not particularly limited so far as it does not adversely affect radical substitution reaction by halogen. For example, carbon tetrachloride, dichloroethane (EDC), etc. can be used. Also, production of α-halogeno-α'-cyano-o-xylenes is possible by gas phase reaction. In this case, α-cyano-o-xylenes are heated and vaporized and reacted with halogen gas under irradiation of ultraviolet rays to produce α-halogeno-α'-cyano-o-xylenes. The reaction system may be any of under pressure, under atmospheric pressure, or under reduced pressure, so far as the reaction mixture can exist in gaseous state. Usually, the reaction is carried out under atmospheric pressure or under reduced pressure. Also, it is possible to carry out the synthesis by diluting the reaction system with gas that does not adversely affect the reaction, such as argon or nitrogen.

The above reaction, no matter whether it is liquid phase reaction or gas phase reaction, is carry out preferably at a conversion (%), as defined by the following equation (3), of the raw material α-cyano-o-xylenes being controlled to 10 to 80%.

$$\text{Conversion} = \{(\alpha\text{-cyano-o-xylene before and after the reaction (mol \% difference)}) \div (\alpha\text{-cyano-o-xylene before the reaction (mol \%)})\} \times 100 \quad (3)$$

If the conversion of α-cyano-o-xylenes is lower than 10%, the productivity is low while the conversion of α-cyano-o-xylenes is higher than 80%, production of dihalogeno form, etc. by-products increases, resulting in that the selectivity (%) of α-halogeno-α'-cyano-o-xylenes as defined by the following equation (4) is decreased.

Selectivity = { (α-halogeno-α'-cyano-o-xylene (mol %)) ÷   (4)
(α-cyano-o-xylene (mol % difference between
before and after reaction))} × 100

After the reaction, the raw material α-cyano-o-xylenes remaining unreacted in the system can be recovered and reused. Although the reaction mixture may be used as it is, it may be purified to a suitable purity by distillation, etc., if desired, before it is used in the reaction.

Step 4: Production Method for Isochromanones by Hydrolysis of α-halogeno-α'-cyano-o-xylene Compound (Preparation of compound of formula (V) from compound of formula (IV))

By heating and hydrolyzing the α-halogeno-α'-cyano-o-xylenes of formula (IV) obtained in the above Step 3 in water or water containing a protic polar solvent, isochromanone compound of formula (V)

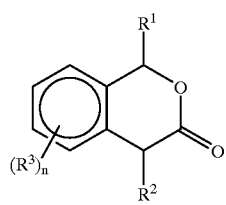
(V)

(wherein the symbols have the same meanings as defined above) can be produced.

As a raw material for the production of isochromanones, usually chlorinated form is used among α-halogeno-α'-cyano-o-xylenes since it is advantageous in view of cost. α-Chloro-α'-cyano-o-xylene can be produced according to the above Step 3. Besides, one produced by reacting α-cyano-o-xylene with sulfuryl chloride by a known method and purified by distillation or crystallization can be used.

As the solvent, water alone is operable. However, it is possible to add protic polar solvents such as lower alcohols (for example, methyl alcohol, ethyl alcohol, propyl alcohol, isopropyl alcohol, and butanol). The protic polar solvents are used in order to increase the affinity of α-halogeno-α'-cyano-o-xylenes for water and carry out hydrolysis reaction more efficiently. When water containing a lower alcohol is used as a solvent, it is necessary to adjust the concentration of alcohol, reaction conditions, etc. since alcohol when in high concentration may cause side reactions with α-halogeno-α'-cyano-o-xylenes.

The amount of water used as a solvent is 1 fold by weight or more and 10 fold by weight or less, preferably 1 fold by weight or more and 5 folds by weight or less, based on the weight of α-halogeno-α'-cyano-o-xylenes. The amount of 1 fold by weight or more and 5 folds by weight or less is industrially advantageous from the point of view of the conversion of α-halogeno-α'-cyano-o-xylenes into isochromanones or productivity of isochromanones based on the amount of solvents used.

To improve productivity, it is advantageous to add to the reaction mixture an inorganic acid such as hydrochloric acid, sulfuric acid or nitric acid and/or Lewis acids, e.g., metal chlorides such as aluminum chloride and zinc chloride, particularly preferably hydrochloric acid in an amount of 0.1 equivalent or more and 5 equivalents or less, preferably 0.3 equivalents or more and 3.5 equivalents or less, based on α-halogeno-α'-cyano-o-xylenes.

The reaction temperature is advantageously 70 to 200° C., preferably 100 to 150° C.

Further, if necessary, the reaction can be carried out under pressure. On this occasion, it is advantageous that the pressure condition is higher than atmospheric pressure and 20 kg/cm² or less, preferably 0.5 kg/cm² or higher and 7 kg/cm² or lower.

The present reaction proceeds usually as two layer reaction or in a state of suspension so that yield can be increased by improving the state of mixing by enhancement of stirring apparatus and so on.

Recovery of isochromanones after the reaction is possible by concentration of reaction mixture or extraction with organic solvents such as ethyl acetate, methylene chloride, toluene, xylene, and ethylbenzene. Depending on the target isochromanones, when there are two layers, i.e., water layer and product layer, it is possible to separate the water layer and remove it. In particular, when the product is 3-isochromanone, the product layer is liquid at 85° C. or higher, and the solubility in water is low so that the target compound can be recovered by the operation of separation. Further, it is possible to obtain high purity 3-isochromanone by distillation purification under reduced pressure.

Thus, isochromanones can be produced in high yield and at high purity by using α-halogeno-α'-cyano-o-xylenes as a raw material in an industrially advantageous manner at low cost, by easy operation and with producing less wastes.

Reaction Scheme 2

Step 5: Production Method for α,α'-dihalogeno-o-xylene Compounds (Preparation of compound of formula (VI) from compound of formula (I))

The raw material o-xylene compound to be used is represented by formula (I)

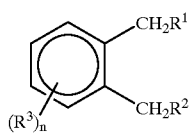
(I)

(wherein, R¹ and R² independently of each other represent hydrogen atom or an alkyl group, R³ represents hydrogen atom, halogen atom, an alkoxy group, a hydroxyalkyl group having 2 or more carbon atoms, or a carboxyl group, and n is an integer of 0 to 4, provided that when n is 2 or more, (R³)s may be the same or different).

Halogenation of the compound of formula (I) using a photocatalyst or radical initiator can give rise to an α,α'-dihalogeno-o-xylene compound of formula (VI)

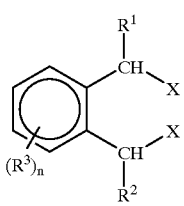
(VI)

(wherein R¹, R², and R³ have the same meanings as defined above and X represents a halogen atom).

For example, o-xylene is chlorinated with chlorine using a photocatalyst or radical initiator and purified by distillation to obtain α,α'-dichloro-o-xylene (Chem. Technik, 20, 38 (1968)).

Step 6: Production Method for α,α'-dihydroxy-o-xylene Compounds (Preparation of compound of formula (VII) from compound of formula (VI))

Using α,α'-dihalogeno-o-xylenes of formula (VI) explained in Step 5, the production method for α,α'-dihydroxy-o-xylene compounds of formula (VII)

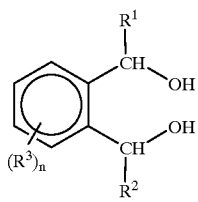

(VII)

(the symbols in the formula have the same meanings as defined above) will be explained.

Preferred examples of $R^1$ and $R^2$ in formula (VI) include a hydrogen atom, a methyl group, an ethyl group, an n-propyl group, etc. Particularly preferred is a hydrogen atom.

$(R^3)$s, which may be the same or different, each represent a hydrogen atom, a chlorine atom, a fluorine atom, a bromine atom, a methoxy group, an ethoxy group, etc. The case where all $(R^3)$s are hydrogen atoms is particularly preferable.

X is, for example, an iodine atom, a bromine atom, or a chlorine atom. From the point of view of cost, a chlorine atom is particularly preferable.

As a specific example of α,α'-dihalogeno-o-xylenes, particularly α,α'-dichloro-o-xylene is preferred.

According to the method of the present step, α,α'-dihydroxy-o-xylene compounds can be prepared by heating α,α'-dihalogeno-o-xylene compounds in the presence of water at pH 8 or lower.

The reaction solvent is preferably water. However, non-polar solvents such as toluene and xylene, polar solvents such as dimethylformamide, dimethyl sulfoxide, and dioxane, and the like general organic solvents may be added. Use of non-polar solvents can prevent production of dimers. Also, use of polar solvents can reduce water. However, alcohols such as methanol and ethanol which react with α,α'-dihalogeno-o-xylenes forming an ether bond and those which are readily hydrolyzed, such as ethyl acetate, are not desirable.

The amount of water to be added to α,α'-dihalogeno-o-xylenes is suitably 10 folds by weight or more. The upper limit is not particularly limited but 20 folds by weight or lower, further 13 to 18 folds by weight, is preferred. When the addition amount is too small, the conversion of α,α'-dihalogeno-o-xylenes is not increased while it is too high, problems in productivity occur such as removal of water. However, when the reaction is carried out by addition of organic solvents to water, sometimes the addition amount of water as described above can be reduced. For example, use of water to which dimethylformamide or dimethyl sulfoxide is added can reduce the addition amount of water to from 2 folds by weight to 10 folds by weight based on α,α'-dihalogeno-o-xylenes.

The reaction temperature is 50 to 130° C., preferably 80 to 110° C. At low temperatures, the reaction proceeds slowly and hence productivity is low. At high temperatures, high-pressure reactor or high temperature thermal medium is necessary, which is industrially disadvantageous.

According as the reaction proceeds, hydrogen halides are generated. If the reaction is continued for many hours in a state where hydrogen halide is at high concentrations, α-chloro-α'-hydroxy form, intermediate, generates condensates as a result of intermolecular dehydrohalogenation, resulting in a decrease in yield. Therefore, it is preferred that the reaction time be selected taking into consideration the conversion of α,α'-dihalogeno-o-xylenes in the system.

The reaction may be carried out while neutralizing the hydrogen halide that is generated during the reaction. However, in this case, at pH 9 or higher, the α-chloro-α'-hydroxy form, intermediate, undergoes intramolecular dehydrohalogenation to produce phthalans of formula (XI) described above to lower yield of α,α'-dihydroxy-o-xylenes, so that pH must be 8 or lower.

The raw material α,α'-dihalogeno-o-xylene compound of formula (VI) has low solubility in water depending on the kinds of its substituents $R^1$ to $R^3$ and even in the reaction which proceeds in systems containing much water, it is sometimes the case that the reaction mixture is in a state separated into two layers. In this case, production of the above-described intermolecular condensates is promoted to decrease yield. This does not depend on the kind of raw materials and when the addition amount of water is small, the reaction mixture is separated into two layers and similar results are obtained. In such case, production of intermolecular condensates can be prevented by addition of organic solvents to lower the concentration of reactants in the organic layer.

As the target α,α'-dihydroxy-o-xylenes (VII), the reaction mixture may be used in the next step as it is without isolation. If necessary, water may be evaporated to concentrate the reaction mixture before use. It is advantageous to carry out concentration operation at 20 to 60° C., preferably 30 to 50° C. When the temperature is too low, the concentration takes a long time whereas when the temperature is too high, production of condensates is promoted, so that both cases are industrially disadvantageous. When pH is too high, phthalan compounds are produced upon concentration to cause loss of α,α'-dihydroxy-o-xylenes, so that concentration may be advantageously conducted after adjusting pH in the neutral regions not exceeding 9, preferably 8, with an alkali agent.

Thus, heating α,α'-dihalogeno-o-xylenes in the presence of water at pH 8 or lower can produce corresponding α,α'-dihydroxy-o-xylenes in an industrially advantageous manner in view of cost and operation. Particularly preferred examples of α,α'-dihydroxy-o-xylenes is α,α'-dihydroxy-o-xylene.

Step 7: Production Method for α-halogeno-α'-hydroxy-o-xylene Compounds (Preparation of compound of formula (VIII) from compound of formula (VII))

Production method for α-halogeno-α'-hydroxy-o-xylenes of formula (VIII)

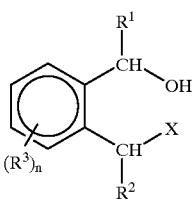

(VIII)

(the symbols in the formula have the same meanings as defined above) characterized by reacting α,α'-dihydroxy-o-xylenes of formula (VII) with a hydrogen halide will be explained.

Preferred examples of $R^1$ and $R^2$ in formula (VII) include a hydrogen atom, a methyl group, an ethyl group, an n-propyl group, etc. Particularly preferred is a hydrogen atom.

Preferred examples of $R^3$ include a hydrogen atom, a chlorine atom, a fluorine atom, a bromine atom, a methoxy group, an ethoxy group, etc. The case where all ($R^3$)s are hydrogen atoms is particularly preferable.

α-Halogeno-α'-hydroxy-o-xylene, which is a raw material for the synthesis of 3-isochromanone, can be produced in high yields by the method of the present step.

α,α'-Dihydroxy-o-xylenes of formula (VII), raw materials, can be produced by the method of the Step 6 according to the present invention. However, those produced by other known methods may also be used.

The solvent when α,α'-dihydroxy-o-xylenes are reacted with a hydrogen halide may be organic solvents or water. In the case of organic solvents, there can be used hydrophobic solvents such as toluene and xylene and polar solvents such as dimethylformamide, dimethyl sulfoxide, and dioxane. Industrially, water is advantageous taking into consideration recovery of solvents, danger upon use, etc. Water and organic solvents can be used in combination. It is particularly preferred that water and hydrophobic organic solvents be used in combination.

The charge concentration of α,α'-dihydroxy-o-xylenes is not particularly limited. However, if it is too low, problem occurs on productivity. As hydrogen halide to be reacted is used preferably hydrogen chloride, which is less expensive. Usage of 0.5 to 3 folds by mole based on α,α'-dihydroxy-o-xylenes is suitable and preferably 1.0 to 2.5 folds by mole. This usage may vary depending on the solvent, reaction temperature and reaction time used. At low molar ratio, the conversion is not increased while at high molar ratio, production of α,α'-dihalogeno-o-xylenes occurs to decrease yield. As for the method of adding hydrogen halide, it may be added en bloc at the initiation of reaction or it may be added continuously. The method of addition may be by blowing dry gas or solutions in water or organic solvents may be used. The concentration of hydrogen halide in the reaction mixture is advantageously 5 to 30%. If the concentration is low, the conversion is decreased while if it is high, high boiling materials are produced as a result of intermolecular dehydrocondensation or dehydrohalogenation condensation between α,α'-dihydroxy-o-xylenes and α-halogeno-α'-hydroxy-o-xylenes, thereby decreasing yield.

The reaction temperature is preferably 80 to 100° C. If it is too low, a decrease in conversion occurs while if it is too high, production of high boiling materials similarly causes a decrease in yield and both cases are undesirable.

The reaction time is determined considering change in products. Lowering temperature or increasing pH to near neutral region with an alkali agent can terminate the reaction. Equilibrium may vary depending on conditions and it is desirable to select various conditions so that α-halogeno-α'-hydroxy-o-xylenes can be obtained in high yields. By-produced α,α'-dihalogeno-o-xylenes similarly undergoes α,α'-dicyanidation in case the reaction proceeds to the step of α-cyanidating α-halogen, so that it is necessary to inhibit the generation thereof as much as possible.

The reaction style of Step 7 may be batch-wise or continuous.

Although explanation has been made on α,α'-dihydroxy-o-xylenes as above, the reaction of Step 7 can be applied to m-xylene compounds and p-xylene compounds. α-Halogeno-α'-hydroxy-m-xylenes can be produced from α,α'-dihydroxy-m-xylenes. Also, α-halogeno-α'-hydroxy-p-xylenes can be produced from α,α'-dihydroxy-p-xylenes. Preferred example of the former is α-chloro-α'-hydroxy-m-xylene and preferred example of the latter is α-chloro-α'-hydroxy-p-xylene.

Step 8: Production Method for α-cyano-α'-hydroxy-o-xylene Compounds (Preparation of compound of formula (IX) from compound of formula (VIII))

Reacting α-halogeno-α'-hydroxy-o-xylenes of formula (VIII) with hydrogen cyanide or salts thereof can produce α-cyano-α'-hydroxy-o-xylenes of formula (IX)

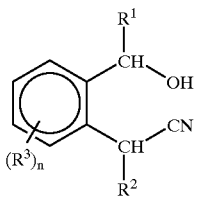

(IX)

(the symbols in the formula have the same meanings as defined above).

Preferred examples of $R^1$ and $R^2$ in formula (VIII) include a hydrogen atom, a methyl group, an ethyl group, an n-propyl group, etc. Particularly preferred is a hydrogen atom. Preferred examples of $R^3$ include a hydrogen atom, a chlorine atom, a fluorine atom, a bromine atom, a methoxy group, an ethoxy group, etc. The case where all ($R^3$)s are hydrogen atoms is particularly preferable.

α-Cyano-α'-hydroxy-o-xylene, which is a raw material for the synthesis of 3-isochromanone, can be produced in high yields by the method of the present step.

α-Halogeno-α'-hydroxy-o-xylenes, raw materials, can be produced by the method of the Step 7 according to the present invention. However, those produced by other known methods may also be used.

When the α-halogeno-α'-hydroxy-o-xylenes obtained by the method of Step 7 above are used as raw materials, the reaction mixture of Step 7 may be used as it is or it may be concentrated and cooled to separate and collect α-halogeno-α'-hydroxy-o-xylenes as solids content before use. Industrially, it is preferred to use the reaction mixture as it is in view of reduction of production steps. Although organic solvents may be added freshly, this is industrially disadvantageous since recover operation and the like are cumbersome. When the reaction mixture of α-halogeno-α'-hydroxy-o-xylenes is used as it is, it is separated into an oil layer in which main component is α-halogeno-α'-hydroxy-o-xylenes and a water layer which contains α,α'-dihydroxy-o-xylenes, raw material, and some α-halogeno-α'-hydroxy-o-xylenes. Therefore, addition of a phase transfer catalyst is more efficient in order to perform cyanidation in a stable manner and in high yield. The phase transfer catalyst may be any of generally used ones. For example, addition of tetrabutylammonium bromide in an amount of 1 to 20% by weight, preferably 3 to 10% by weight, based on α-halogeno-α'-hydroxy-o-xylenes before the reaction is started increases reactivity of cyanidation.

As the cyanidating agent, hydrocyanic acid (prussic acid) or its salts may be used. Industrially used sodium cyanide is preferable since it is economical. Usually, an aqueous solution of it is used. Upon initiation of the reaction, it is preferred that the pH at which cyanidation reaction is practiced be adjusted with an alkali agent such as caustic alkali in advance. The pH in the cyanidation reaction is suitably 5 to 13, preferably 6 to 9. If pH is low, the reaction proceeds slowly and hydrogen cyanide gasifies to decrease rate of reaction, which is industrially disadvantageous. If the pH is high, the portion once halogenated is hydrolyzed again to decrease yield. In addition, dehydrohalogenation occurs in the molecule to produce phthalan compound to decrease yield. Upon cyanidation, when hydrogen cyanide is used as a cyanidating agent, it is desirable that the liquid is dropped or gas is fed into the liquid while controlling the pH with an alkali agent. When salts of hydrogen cyanide, for example, sodium cyanide is used, pH increases so that it is desirable that dropping is carried out while adjusting the pH of the reaction mixture with mineral acid, for example, hydrochloric acid or sulfuric acid.

The reaction temperature is 50 to 120° C., preferably 70 to 100° C. If it is too low, the reactivity is decreased and if it is too high, yield is decreased. The reaction time may vary depending on the reaction temperature and may be determined taking into consideration the conversion of α-halogeno-α'-hydroxy-o-xylenes.

The reaction style of Step 8 may be batch-wise or continuous.

Although explanation has been made on α-cyano-α'-hydroxy-o-xylenes as above, the reaction of Step 8 can be applied to m-xylene compounds and p-xylene compounds. α-Cyano-α'-hydroxy-m-xylenes can be produced from α-halogeno-α'-hydroxy-m-xylenes. Also, α-cyano-α'-hydroxy-p-xylenes can be produced from α-halogeno-α'-hydroxy-p-xylenes. Preferred example of the former is α-cyano-α'-hydroxy-m-xylene and preferred example of the latter is α-cyano-α'-hydroxy-p-xylene.

Step 9: Production Method for Isochromanones by Acid Hydrolysis of α-cyano-α'-hydroxy-o-xylene Compounds (Preparation of compound of formula (V) from compound of formula (IX))

Acid hydrolysis of α-cyano-α'-hydroxy-o-xylene compounds of formula (IX) can produce isochromanone compounds of formula (V)

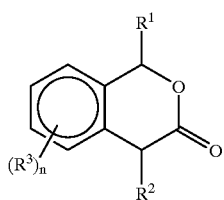

(V)

(the symbols in the formula have the same meanings as defined above).

Preferred examples of $R^1$ and $R^2$ in formula (V) include a hydrogen atom, a methyl group, an ethyl group, an n-propyl group, etc. Particularly preferred is a hydrogen atom. Preferred examples of $R^3$ include a hydrogen atom, a chlorine atom, a fluorine atom, a bromine atom, a methoxy group, an ethoxy group, etc. The case where all $R^3$ is a hydrogen atom is particularly preferable. Preferred example of isochromanones includes 3-isochromanone.

α-Cyano-α'-hydroxy-o-xylenes of formula (IX), raw materials, can be produced by the method of the Step 8 above. However, production method is not limited particularly and those produced by other known methods may also be used.

The hydrolysis with acid in this step can be carried out by adding mineral acid such as sulfuric acid or hydrochloric acid to the cyanidation reaction completed liquid in the Step 8 above and heating the mixture. Sulfuric acid is preferred from the viewpoint of apparatus and costs and is advantageously added 1 to 3 folds by mole, preferably 1.8 to 2.3 folds by mole, based on α-cyano-α'-hydroxy-o-xylenes. If the molar ratio is low, the conversion of α-cyano-α'-hydroxy-o-xylenes is decreased and if it is high, such is industrially disadvantageous.

After the reaction, recovery of isochromanones can be carried out by concentration of reaction mixture or extraction with an organic solvent such as ethyl acetate, toluene, xylene, ethylbenzene, or methylene chloride. When the reaction mixture is separated into two layers, i.e., a water layer and a product layer, depending on the target isochromanones, it is possible to separate and remove the water layer. In particular, when the product is 3-isochromanone, the product layer is liquid at 85° C. or higher, so that solubility in water is low and the target compound can be recovered by separation operation. Further, distillation and purification under reduced pressure can give rise to highly pure 3-isochromanone.

Step 10: Production Method for α-carboxy-α'-hydroxy-o-xylene Compounds (Preparation of compound of formula (X) from compound of formula (IX))

Hydrolysis of α-cyano-α'-hydroxy-o-xylene compound of formula (IX) under an alkaline condition at pH 11 or higher can produce α-carboxy-α'-hydroxy-o-xylenes of formula (X)

(X)

(wherein $R^1$, $R^2$, and $R^3$ have the same meanings as defined above and M represents an alkali metal).

Preferred examples of $R^1$ and $R^2$ in formula (X) include a hydrogen atom, a methyl group, an ethyl group, an n-propyl group, etc. Particularly preferred is a hydrogen atom. Preferred examples of $R^3$ include a hydrogen atom, a chlorine atom, a fluorine atom, a bromine atom, a methoxy group an ethoxy group, etc. The case where all $(R^3)$s are hydrogen atoms is particularly preferable. Examples of M include sodium, potassium, etc.

By the production method in the present step, α-carboxy-α'-hydroxy-o-xylenes, raw material for the synthesis of 3-isochromanone can be produced in high yields.

Preferred examples of $R^1$ and $R^2$ in formula (IX) include a hydrogen atom, a methyl group, an ethyl group, an n-propyl group, etc. Particularly preferred is a hydrogen atom. Preferred examples of $R^3$ include a hydrogen atom, a chlorine atom, a fluorine atom, a bromine atom, a methoxy group, an ethoxy group, etc. The case where all $(R^3)$s are hydrogen atoms is particularly preferable.

α-Cyano-α'-hydroxy-o-xylenes, raw materials, can be produced by the method of the Step 8 above. However, production method is not limited particularly and those produced by other known methods may of course be used.

When the α-cyano-α'-hydroxy-o-xylenes produced by the method of Step 8 above are used as raw materials, they are hydrolyzed under an alkaline condition to synthesize α-carboxy-α'-hydroxy-o-xylenes or salts thereof. It is industrially advantageous to use the reaction mixture as it is.

When a reduction in volume is desired, particularly when the reaction is carried out in aqueous systems, the completed reaction mixture was left to stand and the water layer is discarded and then the layer of α-cyano-α'-hydroxy-o-xylenes is sent to the hydrolysis step. The hydrolysis reaction stoichiometrically requires at least 2 moles of water based on α-cyano-α'-hydroxy-o-xylenes, preferably 3 moles or more.

The hydrolysis at alkali regions is carried out using ammonia or amines as a catalyst. However, industrially, caustic soda is preferred also from the viewpoint of cost. Concentration of alkali is adjusted such that it is always 0.3 to 1.5% by weight in a free state in the system or 1.0 to 1.3 folds by mole of alkali based on α-cyano-α'-hydroxy-o-xylenes is added en bloc before the reaction is carried out. During the reaction, ammonia gas that is generated is neutralized and detoxicated with acid such as sulfuric acid. As for the reaction time, the reaction may be carried out until no ammonia is generated. The reaction may be continued until the conversion reaches saturation while analyzing by HPLC, etc. After completion of the reaction, α-carboxy-α'-hydroxy-o-xylenes exist as alkali salts in the reaction mixture.

α-Carboxy-α'-hydroxy-o-xylenes in alkali regions at pH 9 or higher undergoes dehydrogenodehalogenation within the molecule to by-produce phlathan compounds to decrease yield. Strict control of pH such as maintaining it to preferably pH 6 to 8 is necessary.

Although explanation has been made on α-carboxy-α'-hydroxy-o-xylenes as above, the reaction of Step 10 can be applied to m-xylene compounds and p-xylene compounds. α-Carboxy-α'-hydroxy-m-xylenes can be produced from α-cyano-α'-hydroxy-m-xylenes. Also, α-carboxy-α'-hydroxy-p-xylenes can be produced from α-cyano-α'-hydroxy-p-xylenes. Preferred example of the former is α-carboxy-α'-hydroxy-m-xylene and preferred example of the latter is α-carboxy-α'-hydroxy-p-xylene.

Step 11: Production Method for Isochromanones from Metal Salt of α-carboxy-α'-hydroxy-o-xylene Compounds (Preparation of compound of formula (V) from compound of formula (X))

Addition of an acid to an aqueous solution of a metal salt of α-carboxy-α'-hydroxy-o-xylene compound of formula (X) and hydrolysis at pH 4 or lower, preferably pH 3 or lower, and intramolecular dehydrocondensation can produce isochromanones.

After the reaction, recovery of isochromanones can be carried out by concentration of reaction mixture or extraction with an organic solvent such as ethyl acetate, toluene, xylene and ethylbenzene. When the reaction mixture is separated into two layers, i.e., a water layer and a product layer, depending on the target isochromanones, it is possible to separate and remove the water layer. In particular, when the product is 3-isochromanone, the product layer is liquid at 85° C. or higher, so that solubility in water is low and the target compound can be recovered by separation operation. Further, distillation and purification under reduced pressure can give rise to highly pure 3-isochromanone.

INDUSTRIAL APPLICABILITY

According to the present invention, isochromanone compounds useful as raw materials for drugs and agricultural chemicals can be efficiently produced from o-xylene compounds which are industrially available at low costs (1) through α-halogeno-o-xylene derivatives, α-cyano-o-xylene derivatives and α-halogeno-α'-cyano-o-xylene derivatives, or (2) through α,α'-dihalogeno-o-xylene derivatives, α,α'-dihydroxy-o-xylene derivatives, and α-cyano-α'-hydroxy-o-xylene derivatives and α-halogeno-α'-hydroxy-o-xylene derivatives.

Further, according to the present invention, compounds, which are intermediates for the production of the isochromanone compounds and are useful as intermediates for other drugs and agricultural chemicals can be produced in an industrially advantageous manner.

BEST MODE FOR CARRYING OUT THE INVENTION

Hereinafter, the present invention will be described in more detail by examples and comparative examples. However, the present invention is not limited thereto.

The following examples each was analyzed using a gas chromatography (hereinafter simply referred to as "GC") and a liquid chromatography (hereinafter simply referred to as "HPLC").

<GC Analysis Conditions>
Column: DB-5 manufactured by GL Science
(Length: 30 m, inner diameter: 0.53 mm, film thickness: 1.5 μm)
Column temperature:
100° C. (2 min)→[5° C./min]→150° C. (15 min)
Carrier gas: He
Injection: 310° C.
Transfer ion line temperature: 300° C.
Detector: FID <HPLC Analysis Conditions>:
Column: ODS
Column temperature: 40° C.
Gradient:
0.05% $H_3PO_4$ 30%/MeOH 70%→0.05% $H_3PO_4$ 70%/MeOH 30% (44 min)
Detector: UV 254 nm

EXAMPLE 1 o-Xylene was heated at 160° C. and at atmospheric pressure to vaporize it. The vaporized o-xylene and chlorine gas were fed at flow rates of 28.3 mmol/hr (3 g/hr) and 28.3mmol/hr (1.98 g/hr), respectively, to a reactor (inner diameter 20 mm×1 m) kept at 150° C. By UV irradiation, the reaction was carried out continuously. Gas discharged from the reactor was water-cooled and collected in a Kendall flask. After 0.5 hour from the initiation of collection when the collection amount per unit time became constant, the Kendall flask was replaced another Kendall flask and collection was carried out. A part of the collected product was sampled and the composition of the reaction mixture was analyzed by gas chromatography (GC) analysis. As a result, the conversion of raw material o-xylene was 35%, the yield of α-chloro-o-xylene was 30% (based on o-xylene), and the selectivity of α-chloro-o-xylene was 85%.

The reaction solution which was condensed and recovered was distilled at atmospheric pressure to recover unreacted o-xylene in a yield of 85% (purity 95%). At this time, in the still pot, there remained still residue containing α-chloro-o-xylene. The recovered o-xylene was reused again as a raw material for producing α-chloro-o-xylene. Thus α-chloro-o-xylene was obtained in a total yield of 68% (based on o-xylene)

EXAMPLE 2 o-Xylene was heated at 100° C. and under reduced pressure of 200 mmHg to vaporize it. The vaporized o-xylene and chlorine gas were fed at flow rates of 55 mmol/hr (5.8 g/hr) and 82.5 mmol/hr (5.8 g/hr), respectively, to a reactor (inner diameter 20 mm×1 m) kept at 100° C. By UV irradiation, the reaction was carried out continuously. A part of sample collected was analyzed by GC analysis. As a result, the conversion of raw material o-xylene was 25%, the yield of α-chloro-o-xylene was 22% (based on o-xylene), and the selectivity of α-chloro-o-xylene was 88%.

EXAMPLE 3 o-Xylene was heated at 140° C. At this time, nitrogen gas (18L/hr) was blown from below the liquid surface of o-xylene to promote vaporization. The vaporized o-xylene and chlorine gas were fed at flow rates of 55 mmol/hr (5.8 g/hr) and 82.5 mmol/hr (5.8 g/hr), respectively, to a reactor (inner diameter 20 mm×1 m) kept at 150° C. By UV irradiation, the reaction was carried out continuously. A part of sample collected was analyzed by GC analysis. As a result, the conversion of raw material o-xylene was 28%, the yield of α-chloro-o-xylene was 22% (based on o-xylene), and the selectivity of α-chloro-o-xylene was 79%.

EXAMPLE 4

A condenser tube, a stirring blade and a thermometer were set to a 500-mL-volume four-necked flask and in this reaction device, 86.9 g (0.82 mol) of o-xylene and 2.17 g (0.013 mol) of azobisisobutyronitrile (AIBN) were placed to prepare a mixed solution. After the reaction device was heated to 90° C., chlorine gas was blown therein at a flow rate of 0.378 mol/hr, and the reaction was carried out for 1 hour with stirring. After completion of the reaction, a part of the reaction mixture was sampled. Then, the components of reaction mixture were analyzed by GC. As a result, the conversion of raw material o-xylene was 40%, the yield of α-chloro-o-xylene was 32% (based on o-xylene), and the selectivity of α-chloro-o-xylene was 80%.

The reaction solution which was condensed and recovered was distilled at atmospheric pressure to recover unreacted o-xylene in a yield of 85% (purity 95%). At this time, in the still pot, there remained still residue containing α-chloro-o-xylene. The recovered o-xylene was reused again as a raw material for producing α-chloro-o-xylene. Thus α-chloro-o-xylene was obtained in a total yield of 68% (based on o-xylene)

EXAMPLE 5

A condenser tube, a stirring blade and a thermometer were set to a 500-mL-volume four-necked flask and in this reaction device, 86.9 g (0.82 mol) of o-xylene, 2.17 g (0.013 mol) of AIBN, and 200 g of carbon tetrachloride were placed to prepare a solution. After the reaction device was heated to 80° C., chlorine gas was blown therein at a flow rate of 0.378 mol/hr, and the reaction was carried out for 1 hour with stirring. After completion of the reaction, a part of the reaction mixture was sampled and the components of the reaction mixture were analyzed by GC. As a result, the conversion of raw material o-xylene was 37%, the yield of α-chloro-o-xylene was 32% (based on o-xylene), and the selectivity of α-chloro-o-xylene was 86%.

EXAMPLE 6

A condenser tube, a stirring blade, a thermometer, and a high pressure mercury lamp were set to a 500-mL-volume four-necked flask and in this reaction device, 86.9 g (0.82 mol) of o-xylene and 200 g of carbon tetrachloride were placed to prepare a solution. After irradiating ultraviolet rays from the high-pressure mercury lamp to the reaction mixture, chlorine gas was blown therein at a flow rate of 0.378 mol/hr at room temperature. The reaction was continued for 1 hour with stirring. At this time, the temperature of the reaction mixture was elevated to 70° C. due to heat generation. After completion of the reaction, a part of the reaction mixture was sampled and analyzed for the components by GC analysis. As a result, the conversion of raw material o-xylene was 35%, the yield of α-chloro-o-xylene was 27% (based on o-xylene), and the selectivity of α-chloro-o-xylene was 77%.

EXAMPLE 7

A condenser tube, a stirring blade and a thermometer were set to a 1,000-mL-volume four-necked flask and in this reaction device, 141 g of α-chloro-o-xylene and 7 g of tetrabutylammonium bromide as a phase transfer catalyst to prepare a solution. After the temperature of the solution was elevated to 100° C., 157 g of 32% sodium cyanide aqueous solution was added dropwise over 1 hour while stirring. During the reaction, 10% HCl was added to control pH around 8. After completion of the dropping, stirring was continued for 1 hour at 100° C. and a part of the reaction mixture was sampled and the components of reaction mixture were analyzed by GC. As a result, the conversion of raw material α-chloro-o-xylene was 100%; the yield of α-cyano-o-xylene was 98%. The reaction mixture was separated into 2 layers. After the water layer was removed, α-cyano-o-xylene was purified by distillation.

EXAMPLE 8

A condenser tube, a stirring blade and a thermometer were set to a 1,000-mL-volume four-necked flask and in this reaction device, 131 g (1 mol) of α-cyano-o-xylene prepared in Example 7 and 1.3 g (1 wt % based on α-cyano-o-xylene) of AIBN were dissolved in 300 g of EDC (dichloroethane) as the solvent. The mixed solution was heated at 84° C. to provide a refluxing state and then stirred for 1 hour while blowing chlorine gas at a flow rate of 0.5 mol/hr. After completion of the reaction, a part of the reaction solution was sampled and the components of the reaction solution were analyzed by GC. As a result, the raw material α-cyano-o-xylene was 54 mol %, the objective product α-chloro-α'-cyano-o-xylene was 40 mol % and other components were 6 mol %. From these analysis values, the conversion of α-cyano-o-xylene was 46% and the selectivity to α-chloro-α'-cyano-o-xylene was 86%.

EXAMPLE 9

The same α-cyano-o-xylene as used in Example 8 was vaporized by heating at 250° C. The thus-vaporized α-cyano-o-xylene, chlorine gas and nitrogen gas for dilution were supplied to a reaction vessel heated to 250° C. at a flow rate of 15.3 mmol/hr (2 g/hr), 2.9 mmol/hr (0.21 g/hr) and 300 mmol/hr (8.4 g/hr), respectively, and continuously reacted by irradiating UV. The gas discharged from the reaction vessel was air-cooled and collected in a Kendall flask. After 2 hours passed from the initiation of collection and when the collected amount per unit hour became constant, the flask was exchanged by another Kendall flask (Kendall flask 2) and the gas was collected for 5 hours. The collected amount in Kendall flask 2 was 10.42 g. A part of the product was sampled from this flask and subjected to GC analysis. AS a result, α-cyano-o-xylene was 81.7 mol %, α-chloro-α'-cyano-o-xylene was 15.4 mol % and other components were 2.9 mol %. From these, it was revealed that the conversion of α-cyano-o-xylene was 18.3% and the selectivity to α-chloro-α'-cyano-o-xylene was 84%.

EXAMPLE 10

From the reaction solution of Example 8, EDC was removed using an evaporator. After the removal of EDC, 100 g of the reaction solution (α-cyano-o-xylene: 54 g, α-chloro-α'-cyano-o-xylene: 40 g, others: 6 g) was fractionated using a VIGREAU-CLEISEN type fractionating column (column length: 100 mm). The pressure was constantly 1.5 mmHg and elevating the temperature fractionated four fractions of first fraction, second fraction, third fraction and still residue. Particulars of respective fractions by GC are shown in Table 1.

|  | Distillation Temperature (° C.) | Starting Material (g) | Objective Product (g) | Others (g) |
| --- | --- | --- | --- | --- |
| First fraction | 86–90 | 37.1 | 0.9 | 0.9 |
| Second fraction | 90–100 | 15.1 | 4.7 | 1 |
| Third fraction | 100 | 1.3 | 30 | 1.5 |
| Still residue |  | 0.5 | 4.4 | 2.6 |

Starting material: α-cyano-o-xylene
Objective product: α-chloro-α'-cyano-o-xylene In the third fraction, the objective product α-chloro-α'-cyano-o-xylene was purified to a purity of 90% or more Thus, it is verified that α-chloro-α'-cyano-o-xylene can be purified from the reaction solution by distillation. Also, it is verified that the starting material can be recovered.

EXAMPLE 11

A stirring unit, a thermometer and a pressure gauge were set to a 50-mL autoclave. Thereto, 10 g (purity: 100%, 60.4 mmol) of α-chloro-α'-cyano-o-xylene synthesized in the same manner as in Example 10, 50 g of water and 6.3 g of concentrated hydrochloric acid were added and reacted while stirring at a reaction bath temperature of 150° C. and an autoclave internal pressure of 5 kg/cm² for 3 hours. The reaction proceeded as a two-layer reaction.

After completion of the reaction, the concentration of 3-isochromanone was analyzed by GC analysis and then the yield of 3-isochromanone was calculated. As a result, the yield was found to be 95% based on α-chloro-α'-cyano-o-xylene. At this time, the conversion ratio of α-chloro-α'-cyano-o-xylene was 100% and the by-product compound (α-hydroxy-α'-cyano-o-xylene) where the halogen moiety was hydrolyzed was produced in a yield of 1.6%.

When the reaction solution temperature was still in the vicinity of from 80 to 100° C., the aqueous layer was removed by liquid separation, and thereby 3-isochromanone could be obtained. Furthermore, by cooling the reaction solution to about room temperature, 3-chromanone could be recovered as crystals. At this time, ammonium chloride is produced in the form of crystal but could be easily removed by washing the crystals with water.

EXAMPLE 12

A stirring unit, a thermometer and a pressure gauge were set to a 50-mL autoclave. Thereto, 10 g (60.4 mmol) of α-chloro-α'-cyano-o-xylene obtained in the same manner as in Example 10 and 50 g of water were added and reacted while stirring at a reaction bath temperature of 150° C. and an autoclave internal pressure of 5 kg/cm² for 3 hours. The reaction proceeded as a two-layer reaction.

After the completion of reaction, the concentration of 3-isochromanone was analyzed by GC analysis and then the yield of 3-isochromanone was calculated. As a result, the yield was found to be 75% based on α-chloro-α'-cyano-o-xylene. At this time, the conversion ratio of α-chloro-α'-cyano-o-xylene was 100% and the by-product α-hydroxy-α'-cyano-o-xylene was produced in a yield of 2.2%. Furthermore, as a result of the HPLC analysis, α-carboxy-α'-hydroxy-o-xylene and α-aminocarboxy-α'-hydroxy-o-xylene were found to be present as by-products in a concentration of 18% based on α-chloro-α'-cyano-o-xylene.

EXAMPLE 13

A condenser tube, a stirring blade and a thermometer were set to a 50-mL four-necked flask. Thereto, 10 g (60.4 mmol) of α-chloro-α'-cyano-o-xylene synthesized and purified in the same manner as in Example 10, 50 g of water and 6.3 g of concentrated hydrochloric acid were added and reacted while stirring at a reaction bath temperature of 130° C. (reaction solution temperature: 100° C.) for 6 hours. The reaction proceeded as a two-layer reaction.

After the completion of reaction, the concentration of 3-isochromanone was analyzed by GC analysis and then the yield of 3-isochromanone was calculated, as a result, the yield was found to be 76% based on α-chloro-α'-cyano-o-xylene. At this time, the conversion of α-chloro-α'-cyano-o-xylene was 98% and the by-product compound where the halogen moiety was hydrolyzed was produced in a yield of 8%. Furthermore, as a result of the HPLC analysis, α-carboxy-α'-hydroxy-o-xylene and α-aminocarboxy-α'-hydroxy-o-xylene were found to be produced in a yield of 11% based on α-chloro-α'-cyano-o-xylene.

COMPARATIVE EXAMPLE 1

A condenser tube, a stirring blade and a thermometer were set to a 50-mL four-necked flask. Thereto, 10 g (60.4 mmol) of α-chloro-α'-cyano-o-xylene synthesized and 48 g of 5% sodium hydroxide were added and reacted while stirring at a reaction bath temperature of 130° C. (reaction solution temperature: 100° C.) for 6 hours.

After the completion of reaction, the pH of the reaction solution was adjusted to be acidic by 10% hydrochloric acid. Thereafter, the concentration of 3-isochromanone was analyzed by GC analysis and then the yield of 3-isochromanone was calculated, as a result, the yield was found to be 3% based on α-chloro-α'-cyano-o-xylene. At this time, production of a material having unknown components was found.

EXAMPLE 14

A condenser tube, a stirring blade and a thermometer were set to a 500-mL-volume four-necked flask and in this reaction device, 86.9 g (0.82 mol) of o-xylene and 2.17 g (0.013 mol) of AIBN were placed to prepare a mixed solution. After the reaction device was heated to 90° C., chlorine gas was blown therein at a flow rate of 0.378 mol/hr, and the reaction was carried out for 4 hour with stirring. After completion of the reaction, a part of the reaction mixture was sampled. Then, the components of reaction mixture were analyzed by GC. As a result, the conversion of raw material o-xylene was 99.7%, the yield of α,α'-dichloro-o-xylene was 50.5% (based on o-xylene), and the selectivity of α,α'-dichloro-o-xylene was 50.7%. At this time, α-chloro-o-xylene was obtained in a yield of 30%

(based on o-xylene), α,α-dichloro-o-xylene was obtained in a yield of 7%, and α,α,α'-trichloro-o-xylene was obtained in a yield of 9%.

EXAMPLE 15

α,α'-Dichloro-o-xylene (87.5 g, 0.5 mol) and water (1300 g, 72 mol) were placed in a 2000-mL four-neck flask equipped with a condenser tube, a stirring blade, and a thermometer, and the mixture was stirred at 100° C. for four hours. When reaction was completed, the reaction mixture was at pH 1 or lower and assumed a homogeneous layer. The reaction mixture was sampled while stirring and analyzed by GC. The yield of α,α'-dihydroxy-o-xylene was calculated to be 90% based on α,α'-dichloro-o-xylene serving as a raw material. The conversion of α,α'-dichloro-o-xylene was 99%, and α-chloro-α'-hydroxy-o-xylene (1%), phthalan (3%), and an intermolecular condensation product (2%) were formed as by-products.

EXAMPLE 16

The procedure of Example 15 was performed except that the pH of the reaction mixture was regulated to 7 by use of sodium hydroxide. When reaction was completed, the reaction mixture assumed a homogeneous layer. The reaction mixture was sampled for analysis. The yield of α,α'-dihydroxy-o-xylene was calculated to be 92% based on α,α'-dichloro-o-xylene serving as a raw material. The conversion of α,α'-dichloro-o-xylene was 99%, and α-chloro-α'-hydroxy-o-xylene (1%), phthalan (4%), and a high-boiling point compound of unknown composition (1%) were formed as by-products.

EXAMPLE 17

α,α'-Dichloro-o-xylene (87.5 g, 0.5 mol), water (360 g, 20 mol), and dimethyl sulfoxide (1000 g, 13 mol) were placed in a 2000-mL four-neck flask equipped with a condenser tube, a stirring blade, and a thermometer, and the mixture was stirred at 100° C. for four hours. The reaction mixture was sampled for analysis. The yield of α,α'-dihydroxy-o-xylene was calculated to be 92% based on α,α'-dichloro-o-xylene serving as a raw material. The conversion of α,α'-dichloro-o-xylene was 99%, and α-chloro-α'-hydroxy-o-xylene (1%), phthalan (2%), and an intermolecular condensation product (1%) were formed as by-products. The pH of the reaction mixture upon completion of the reaction was 1 or lower.

COMPARATIVE EXAMPLE 2

The procedure of Example 15 was performed except that the pH of the reaction mixture was regulated to 12 by use of sodium hydroxide. The reaction mixture was sampled for analysis. Formation of α,α'-dihydroxy-o-xylene was not observed. Instead, phthalan was formed at a yield of 96% based on α,α'-dichloro-o-xylene.

EXAMPLE 18

A reagent, α,α'-dihydroxy-o-xylene, produced by Aldrich Co. (69.5 g, 0.5 mol) was placed in a 500-mL four-neck flask equipped with a condenser tube, a stirring blade, a thermometer, and a dropping funnel, and 35% hydrochloric acid (100 g, 1.0 mol) was added thereto. The mixture was stirred at 70° C. for one hour. After completion of reaction, the reaction mixture was allowed to stand, so that two-separated layers were formed. The reaction was analyzed through GC while stirring again during sampling. From the obtained concentration of α-chloro-α'-hydroxy-o-xylene, the yield of α-chloro-α'-hydroxy-o-xylene was calculated to be 91% based on α,α'-dihydroxy-o-xylene. The conversion of α,α'-dihydroxy-o-xylene was 99%, and α,α'-dichloro-o-xylene (5%) and phthalan (2%) were formed as by-products.

EXAMPLE 19

The reaction mixture of Example 18 was cooled to 20° C., gradually neutralized to pH 7 with a 1N caustic soda solution, and concentrated to 110 g by use of a rotary evaporator. Tetrabutylammonium bromide (product of Tokyo Kasei Co.) (7 g) was added thereto to thereby adjust the pH to 8. After the mixture was stirred and heated to 80° C., dropping of a 30% sodium cyanide solution (114 g, 0.7 mol) placed in the dropping funnel was started. During the dropping, pH was maintained at 8 by addition of concentrated hydrochloric acid and the dropping was conducted over four hours and the reaction mixture was stirred at 80° C. for additional one hour. After completion of reaction, the reaction mixture was allowed to stand, and two separate layers were formed. The reaction mixture was analyzed by GC while stirring again during sampling. The yield of α-cyano-α'-hydroxy-o-xylene was calculated to be 75% based on α,α'-dihydroxy-o-xylene.

EXAMPLE 20

The reaction mixture of Example 19 was heated to 100° C., and a 48% caustic soda solution (67 g, 0.8 mol) was added thereto. The resultant mixture was allowed to react for four hours. The reaction mixture, exhibiting a brown color, was analyzed by HPLC, to thereby determine the yield of an Na salt of α-carboxy-α'-hydroxy-o-xylene. The yield based on α,α'-dihydroxy-o-xylene was 81%.

EXAMPLE 21

The reaction mixture of Example 20 was allowed to react at 100° C. for four hours while adjusting pH at 2 with concentrated hydrochloric acid. After the reaction was completed and the mixture was allowed to stand, the mixture separated into two layers. While stirring, the reaction mixture was sampled and the yield of 3-isochromanone was obtained by GC analysis. The yield based on α,α'-dihydroxy-o-xylene was 78%.

EXAMPLE 22

A procedure almost identical with that of Examples 18 or 19 was carried out, to thereby produce a reaction mixture containing α-cyano-α'-hydroxy-o-xylene (yield based on α,α'-dihydroxy-o-xylene of 76%). The mixture was allowed to stand at 80° C., and the upper aqueous layer was removed by use of a Komagome pipette. To the remainder of the mixture, 98% sulfuric acid (60 g, 0.6 mol) was added, and the resultant mixture was allowed to react at 100–110° C. for five hours. The mixture was analyzed by GC, to thereby determine the yield of 3-isochromanone. The yield based on α,α'-dihydroxy-o-xylene was 75%.

EXAMPLE 23

A reagent, α,α'-dihydroxy-o-xylene produced by Aldrich Co. (34.8 g, 0.25 mol), was placed in a 500-mL four-neck flask equipped with a condenser tube, a stirring blade, a thermometer, and a dropping funnel, and 35% hydrochloric acid (50 g, 0.5 mol) was added thereto. The mixture was stirred at 70° C. for one hour. After completion of reaction, the reaction mixture was allowed to stand, and two separate layers were formed. The reaction was analyzed by GC while stirring again during sampling. From the obtained concentration of α-chloro-α'-hydroxy-o-xylene, the yield of α-chloro-α'-hydroxy-o-xylene was calculated to be 93% based on α,α'-dihydroxy-o-xylene. Hereafter, the procedure of Examples 19 and 20 was carried out, to thereby produce an Na salt of α-carboxy-α'-hydroxy-o-xylene. The reaction mixture was analyzed by HPLC, to thereby determine the yield of an Na salt of α-carboxy-α'-hydroxy-o-xylene. The yield based on α,α'-dihydroxy-o-xylene was 85%.

EXAMPLE 24

A reagent, α,α'-dihydroxy-o-xylene produced by Aldrich Co. (27.8 g, 0.2 mol), was placed in a 300-mL four-neck flask equipped with a condenser tube, a stirring blade, a thermometer, and a dropping funnel, and toluene (20-mL) and 35% hydrochloric acid (30 g, 0.3 mol) were added thereto. The mixture was stirred at 70° C. for two hours. After completion of reaction, the reaction was analyzed by GC while stirring during sampling. From the obtained concentration of α-chloro-α'-hydroxy-o-xylene, the yield of α-chloro-α'-hydroxy-o-xylene was calculated to be 95% based on α,α'-dihydroxy-o-xylene. This reaction mixture was cooled to 20° C., neutralized to pH 7 with a 1N caustic soda solution, and concentrated to 60 g by use of a rotary evaporator. Through the concentration step, toluene was almost completely removed. The resultant mixture was placed into the reactor again, and cyanidation and hydrolysis were carried out in manners similar to that described in Examples 19 and 20, respectively. The reaction mixture was analyzed by HPLC, to thereby determine the yield of an Na salt of α-carboxy-α'-hydroxy-o-xylene. The yield based on α,α'-dihydroxy-o-xylene was 83%.

What is claimed is:

1. A method for producing isochromanone compound of formula (V)

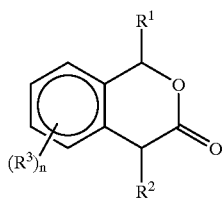

(V)

wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different, which comprises the steps of:

subjecting an o-xylene compound of formula (I)

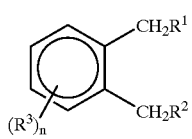

(I)

wherein the symbols have the same meanings as defined above, to halogenation reaction in gas phase or liquid phase to prepare an α-halogeno-o-xylene compound of formula (II)

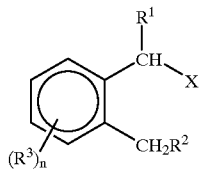

(II)

wherein X represents a halogen atom, and other symbols have the same meanings as defined above;

reacting the compound of formula (II) above with hydrogen cyanide or salts thereof to prepare an α-cyano-o-xylene compound of formula (III)

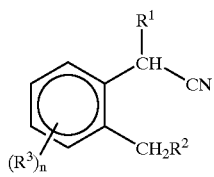

(III)

wherein the symbols have the same meanings as defined above;

reacting the compound of formula (III) with halogen to prepare an α-halogeno-α'-cyano-o-xylene compound of formula (IV)

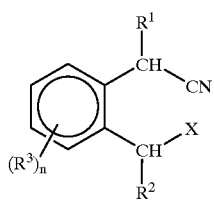

(IV)

wherein the symbols have the same meanings as defined above; and hydrolyzing the compound of formula (IV) in water or water containing a protic polar solvent under acidic condition.

2. A method for producing isochromanone compound of formula (V)

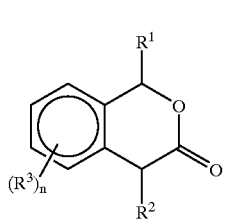

(V)

wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different, comprising:

hydrolyzing an α-halogeno-α'-cyano-o-xylene of formula (IV)

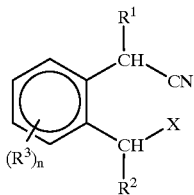

(IV)

wherein X represents a halogen atom and the other symbols have the same meanings as defined above, in water or water containing a protic polar solvent under acidic condition.

3. The method for producing isochromanone compound as claimed in claim 2, wherein the protic polar solvent is a lower alcohol.

4. The method for producing isochromanone compound as claimed in claim 2, comprising: hydrolyzing by adding an inorganic acid and/or a metal chloride are added and hydrolysis reaction is carried out.

5. The method for producing isochromanone compound as claimed in claim 4, wherein the metal chloride is aluminum chloride or zinc chloride.

6. The method for producing isochromanone compound as claimed in claim 4, wherein addition amount of the inorganic acid and/or the metal chloride are 0.1 to 5 equivalents per α-halogeno-α'-cyano-o-xylene compound.

7. The method for producing isochromanone compound as claimed in claim 2, comprising: hydrolyzing under heating conditions at 70 to 200° C.

8. The method for producing isochromanone compound as claimed in claim 2, comprising: hydrolyzing under pressurized conditions at atmospheric pressure to 20 kg/cm².

9. The method for producing isochromanone compound as claimed in claim 2, wherein the α-halogeno-α'-cyano-o-xylene compound of formula (IV) is α-chloro-α'-cyano-o-xylene and the isochromanone compound of formula (V) is 3-isochromanone.

10. A method for producing α-halogeno-α'-cyano-o-xylene compound of formula (IV)

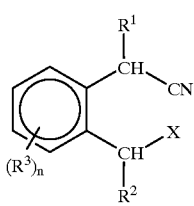

(IV)

wherein R¹ and R² independently of each other represent hydrogen atom or an alkyl group, R³ represents hydrogen atom, halogen atom, an alkoxy group, a hydroxyalkyl group having 2 or more carbon atoms, or a carboxyl group, and n is an integer of 0 to 4, provided that when n is 2 or more, (R³)s may be the same or different and X represents a halogen atom, comprising:

reacting an α-cyano-o-xylene compound of formula (III)

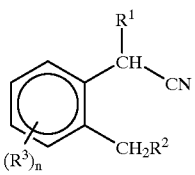

(III)

wherein the symbols have the same meanings as defined above with halogen.

11. The method for producing α-halogeno-α'-cyano-o-xylene compound as claimed in claim 10, comprising: reacting in liquid phase by diluting the α-cyano-o-xylene compound with an organic solvent.

12. The method for producing α-halogeno-α'-cyano-o-xylene compound as claimed in claim 10, wherein the reaction is carried out in the presence of a radical initiator or under irradiation of ultraviolet rays.

13. The method for producing α-halogeno-α'-cyano-o-xylene compound as claimed in claim 10, comprising: reacting in gas phase by vaporing the α-cyano-o-xylene compound.

14. The method for producing α-halogeno-α'-cyano-o-xylene compound as claimed in claim 10, wherein the α-cyano-o-xylene compound is α-cyano-o-xylene and the α-halogeno-α'-cyano-o-xylene compound is α-halogeno-α'-cyano-o-xylene.

15. A method for producing isochromanone compound of formula (V)

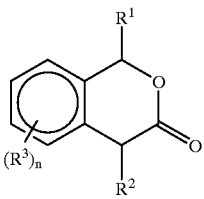

(V)

wherein R¹ and R² independently of each other represent hydrogen atom or an alkyl group, R³ represents hydrogen atom, halogen atom, an alkoxy group, a hydroxyalkyl group having 2 or more carbon atoms, or a carboxyl group, and n is an integer of 0 to 4, provided that when n is 2 or more, (R³)s may be the same or different, which comprises the steps of:

subjecting an o-xylene compound of formula (I)

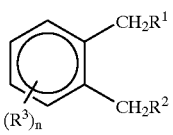

(I)

wherein the symbols have the same meanings as defined above, to halogenation reaction in gas phase or liquid phase to prepare an α,α'-dihalogeno-o-xylene compound of formula (VI)

(VI)

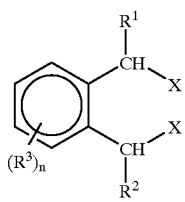

wherein X represents a halogen atom, and other symbols have the same meanings as defined above;

heating the compound of (VI) in the presence of water at pH 8 or lower to prepare an α,α'-dihydroxy-o-xylene compound of formula of formula (VII)

(VII)

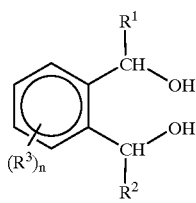

wherein the symbols have the same meanings as defined above;

reacting the compound of formula (VII) with hydrogen halide to prepare an α-halogeno-α'-hydroxy-o-xylene compound of formula (VIII)

(VIII)

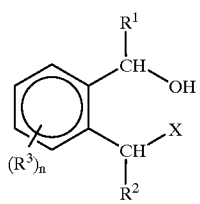

wherein X represents a halogen atom and the other symbols have the same meanings as defined above;

reacting the compound of formula (VIII) with hydrogen cyanide or salts thereof to prepare an α-cyano-α'-hydroxy-o-xylene compound of formula (IX)

(IX)

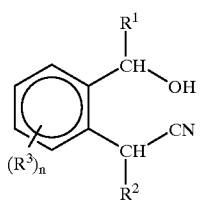

wherein the symbols have the same meanings as defined above; and acid hydrolyzing the compound of formula (IX).

16. A method for producing an isochromanone compound of formula (V)

(V)

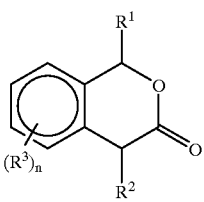

wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different, comprising:

acid hydrolyzing a compound of formula (IX)

(IX)

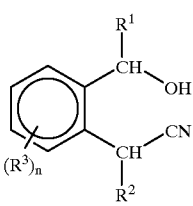

wherein the symbols have the same meanings as defined above.

17. The method for producing an isochromanone compound as claimed in claim 16, wherein an α-cyano-α'-hydroxy-o-xylene compound of formula (IX)

(IX)

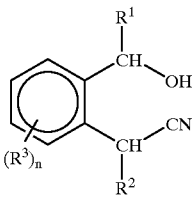

wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different, obtained by reacting a compound of formula (VIII)

(VIII)

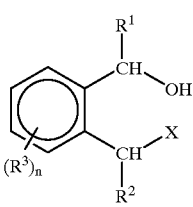

wherein X represents a halogen atom and the other symbols have the same meanings as defined above, with hydrogen cyanide or salts thereof is used.

18. A method for producing an α-cyano-α'-hydroxy-o-xylene compound of formula (IX)

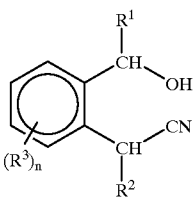
(IX)

wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different, comprising the step of:
reacting an α-halogeno-α'-hydroxy-o-xylene compound of formula (VIII)

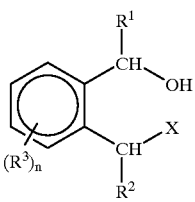
(VIII)

wherein X represents a halogen atom and the other symbols have the same meanings as defined above, with hydrogen cyanide or salts thereof.

19. The method for producing an α-cyano-α'-hydroxy-o-xylene compound as claimed in claim 18, wherein an α-halogeno-α'-hydroxy-o-xylene compound of formula (VIII) obtained by reacting a compound of formula (VII)

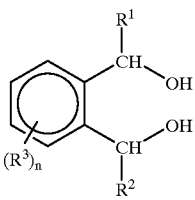
(VII)

wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different, with hydrogen halide is used.

20. The method for producing an α-cyano-α'-hydroxy-o-xylene compound as claimed in claim 18, comprising: reacting with hydrogen cyanide or salts thereof at a pH in the range of 4 to 10.

21. The method for producing an α-cyano-α'-hydroxy-o-xylene compound as claimed in claim 18, comprising: reacting with hydrogen cyanide or salts thereof by addition of a phase transfer catalyst.

22. The method for producing an α-cyano-α'-hydroxy-o-xylene compound as claimed in claim 18, wherein the α-halogeno-α'-hydroxy-o-xylene compound is α-halogeno-α'-hydroxy-o-xylene.

23. A method for producing an α-halogeno-α'-hydroxy-o-xylene compound of formula (VII)

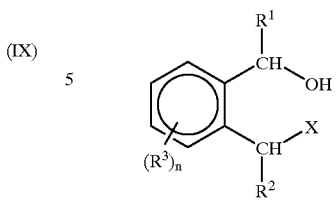
(VIII)

wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different and X represents a halogen atom, comprising the step of reacting a α,α'-dihydroxy-o-xylene compound of formula (VII)

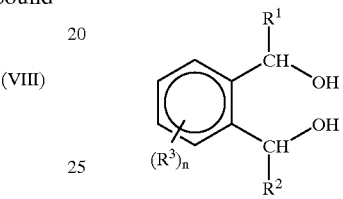
(VII)

wherein the symbols have the same meanings as defined above, with hydrogen halide.

24. The method for producing an α-halogeno-α'-hydroxy-o-xylene compound as claimed in claim 23, wherein the reaction is carried out in an aqueous solution.

25. The method for producing an α-halogeno-α'-hydroxy-o-xylene compound as claimed in claim 24, wherein a hydrophobic organic solvent is used in combination.

26. The method for producing an α-halogeno-α'-hydroxy-o-xylene compound as claimed in claim 24, wherein water is used 5 to 15 folds by mole based on the α,α'-dihydroxy-o-xylene compound.

27. The method for producing an α-halogeno-α'-hydroxy-o-xylene compound as claimed in claim 23, wherein, the hydrogen halide is used 1.5 to 3 folds by mole based on the α,α'-dihydroxy-o-xylene compound for the reaction.

28. The method for producing an α-halogeno-α'-hydroxy-o-xylene compound as claimed in claim 23, wherein the hydrogen halide is hydrogen chloride.

29. The method for producing an α-halogeno-α'-hydroxy-o-xylene compound as claimed in claim 23, wherein the α,α'-dihydroxy-o-xylene compound of formula (VII) is α,α'-dihydroxy-o-xylene and the α-halogeno-α'-hydroxy-o-xylene compound of formula (VIII) is α-chloro-α'-hydroxy-o-xylene.

30. A method for producing an α,α'-dihydroxy-o-xylene compound of formula (VII)

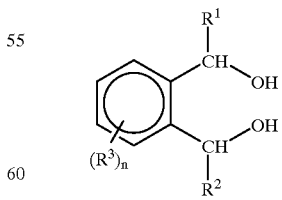
(VII)

wherein $R^1$ and $R^2$ independently of each other represent hydrogen atom or an alkyl group, $R^3$ represents hydrogen atom, halogen atom, an alkoxy group, a hydroxyalkyl group having 2 or more carbon atoms, or a carboxyl group, and n is an integer of 0 to 4, provided that when n is 2 or more, $(R^3)$s may be the same or different, comprising:

heating an α,α'-dihalogeno-o-xylene compound of formula (VI)

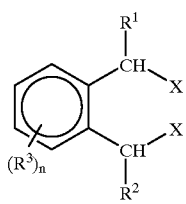

wherein X represents a halogen atom and the other symbols have the same meanings as defined above, at pH 8 or less in the presence of water.

31. The method for producing an α,α'-dihydroxy-o-xylene compound as claimed in claim 30, wherein the reaction is carried out at pH 8 or lower.

32. The method for producing an α,α'-dihydroxy-o-xylene compound as claimed in claim 30, wherein water is 10 folds by weight or more based on the α,α'-dihalogeno-o-xylene compound.

33. The method for producing an α,α'-dihydroxy-o-xylene compound as claimed in claim 30, wherein the reaction is carried out in an aqueous solution.

34. The method for producing an α,α'-dihydroxy-o-xylene compound as claimed in claim 30, wherein the α,α'-dihalogeno-o-xylene compound of formula (VI) is α,α'-dichloro-o-xylene and the α,α'-dihydroxy-o-xylene compound of formula (VIII) is α,α'-dihydroxy-o-xylene.

* * * * *